United States Patent
Felix et al.

(10) Patent No.: US 11,944,289 B2
(45) Date of Patent: Apr. 2, 2024

(54) ARTICULATING SURGICAL INSTRUMENTS

(71) Applicant: C.R. Bard, Inc., Murray Hill, NJ (US)

(72) Inventors: Augustus Felix, Cranston, RI (US); Derek J. Leatzow, Chicago, IL (US); Nathan Stewart Cauldwell, Hope, RI (US); Derek Affonce, Uxbridge, MA (US); Kevin J. Ranucci, Warwick, RI (US); Tomas Matusaitis, Chicago, IL (US); Alan Bachman, Orange, CT (US)

(73) Assignee: C.R. Bard, Inc., Murray Hill, NJ (US)

( * ) Notice: Subject to any disclaimer, the term of this patent is extended or adjusted under 35 U.S.C. 154(b) by 181 days.

(21) Appl. No.: 17/400,511

(22) Filed: Aug. 12, 2021

(65) Prior Publication Data

US 2021/0369265 A1  Dec. 2, 2021

Related U.S. Application Data

(62) Division of application No. 15/867,035, filed on Jan. 10, 2018, now Pat. No. 11,103,234.

(51) Int. Cl.
*A61B 17/068* (2006.01)
*A61B 17/00* (2006.01)
(Continued)

(52) U.S. Cl.
CPC .... *A61B 17/0469* (2013.01); *A61B 17/00234* (2013.01); *A61B 17/0487* (2013.01);
(Continued)

(58) Field of Classification Search
CPC .. A61B 2017/00309; A61B 2017/2908; A61B 1/0055; A61B 17/0469;
(Continued)

(56) References Cited

U.S. PATENT DOCUMENTS

| 3,802,440 A | 4/1974 | Salem et al. |
| 5,797,537 A | 8/1998 | Oberlin et al. |

(Continued)

FOREIGN PATENT DOCUMENTS

| CN | 101516273 A | 8/2009 |
| JP | 2011-517290 | 6/2011 |

(Continued)

OTHER PUBLICATIONS

International Search Report and Written Opinion for International Application No. PCT/US2019/012129, dated May 27, 2019.

*Primary Examiner* — Kathleen S Holwerda
(74) *Attorney, Agent, or Firm* — Wolf, Greenfield & Sacks, P.C.

(57) ABSTRACT

Articulating surgical instruments are disclosed. In one embodiment, a surgical instrument may include an elongated shaft assembly including an articulable portion moveable between a non-articulated configuration and an articulated configuration. First and second articulating shafts of the elongated shaft assembly may be coaxially arranged and axially fixed at an attachment point located distally from the articulable portion. Proximal portions of the first and second articulating shafts may be displaceable in opposing directions to articulate the articulable portion from the non-articulated configuration to the articulated configuration. In another embodiment, an articulation control may be movable from a first position to a second position to move an articulation lock from a locked configuration to an unlocked configuration to selectively permit articulation of a surgical instrument. The articulation lock also may be movable from the second position to a third position to articulate the surgical instrument.

26 Claims, 16 Drawing Sheets

(51) Int. Cl.
*A61B 17/04* (2006.01)
*A61B 17/10* (2006.01)
*A61B 17/29* (2006.01)
*A61B 17/32* (2006.01)
*A61B 1/005* (2006.01)
*A61B 17/02* (2006.01)
*A61B 17/064* (2006.01)

(52) U.S. Cl.
CPC ............ *A61B 17/068* (2013.01); *A61B 17/10* (2013.01); *A61B 17/2909* (2013.01); *A61B 17/320016* (2013.01); *A61B 1/0055* (2013.01); *A61B 2017/00309* (2013.01); *A61B 17/0218* (2013.01); *A61B 2017/0488* (2013.01); *A61B 2017/0647* (2013.01); *A61B 2017/2908* (2013.01); *A61B 2017/2929* (2013.01); *A61B 2017/2932* (2013.01)

(58) Field of Classification Search
CPC ............ A61B 17/0487; A61B 17/2909; A61B 17/320016; A61M 25/0138; A61M 25/0053; A61M 25/0013
See application file for complete search history.

(56) References Cited

U.S. PATENT DOCUMENTS

| | | | |
|---|---|---|---|
| 5,851,212 | A | 12/1998 | Zirps et al. |
| 6,146,338 | A | 11/2000 | Gardeski et al. |
| 6,746,422 | B1 | 6/2004 | Noriega et al. |
| 7,637,903 | B2 | 12/2009 | Lentz et al. |
| 7,785,252 | B2 | 8/2010 | Danitz et al. |
| 8,251,977 | B2 | 8/2012 | Partlett |
| 8,323,241 | B2 | 12/2012 | Salahieh et al. |
| 8,684,953 | B2 | 4/2014 | Cabiri |
| 9,339,271 | B2 | 5/2016 | Ranucci et al. |
| 11,013,502 | B2 | 5/2021 | Ranucci et al. |
| 11,103,234 | B2 | 8/2021 | Felix et al. |
| 11,134,928 | B2 | 10/2021 | Felix et al. |
| 11,419,603 | B2 | 8/2022 | Felix et al. |
| 2003/0191516 | A1 | 10/2003 | Weldon et al. |
| 2006/0229665 | A1 | 10/2006 | Wales et al. |
| 2006/0241564 | A1 | 10/2006 | Corcoran et al. |
| 2010/0331776 | A1 | 12/2010 | Salahieh et al. |
| 2011/0040308 | A1 | 2/2011 | Cabrera et al. |
| 2012/0277730 | A1* | 11/2012 | Salahieh ............ A61B 1/00135 604/528 |
| 2014/0263544 | A1 | 9/2014 | Ranucci et al. |
| 2014/0276965 | A1* | 9/2014 | Ranucci ............ A61B 17/064 606/139 |
| 2014/0276966 | A1* | 9/2014 | Ranucci ........... A61B 17/00234 606/139 |
| 2015/0099997 | A1 | 4/2015 | Cabiri |
| 2016/0249901 | A1 | 9/2016 | Ranucci et al. |
| 2018/0049873 | A1* | 2/2018 | Manash ............ A61M 25/0068 |
| 2019/0209158 | A1 | 7/2019 | Felix et al. |
| 2021/0236106 | A1 | 8/2021 | Ranucci et al. |
| 2022/0338864 | A1 | 10/2022 | Felix et al. |

FOREIGN PATENT DOCUMENTS

| | | |
|---|---|---|
| JP | 2014-515641 A | 7/2014 |
| JP | 2016-510651 A | 4/2016 |
| WO | WO 2012/125635 A2 | 9/2012 |
| WO | WO 2016/138443 A2 | 9/2016 |
| WO | WO 2016/205163 A1 | 12/2016 |

* cited by examiner

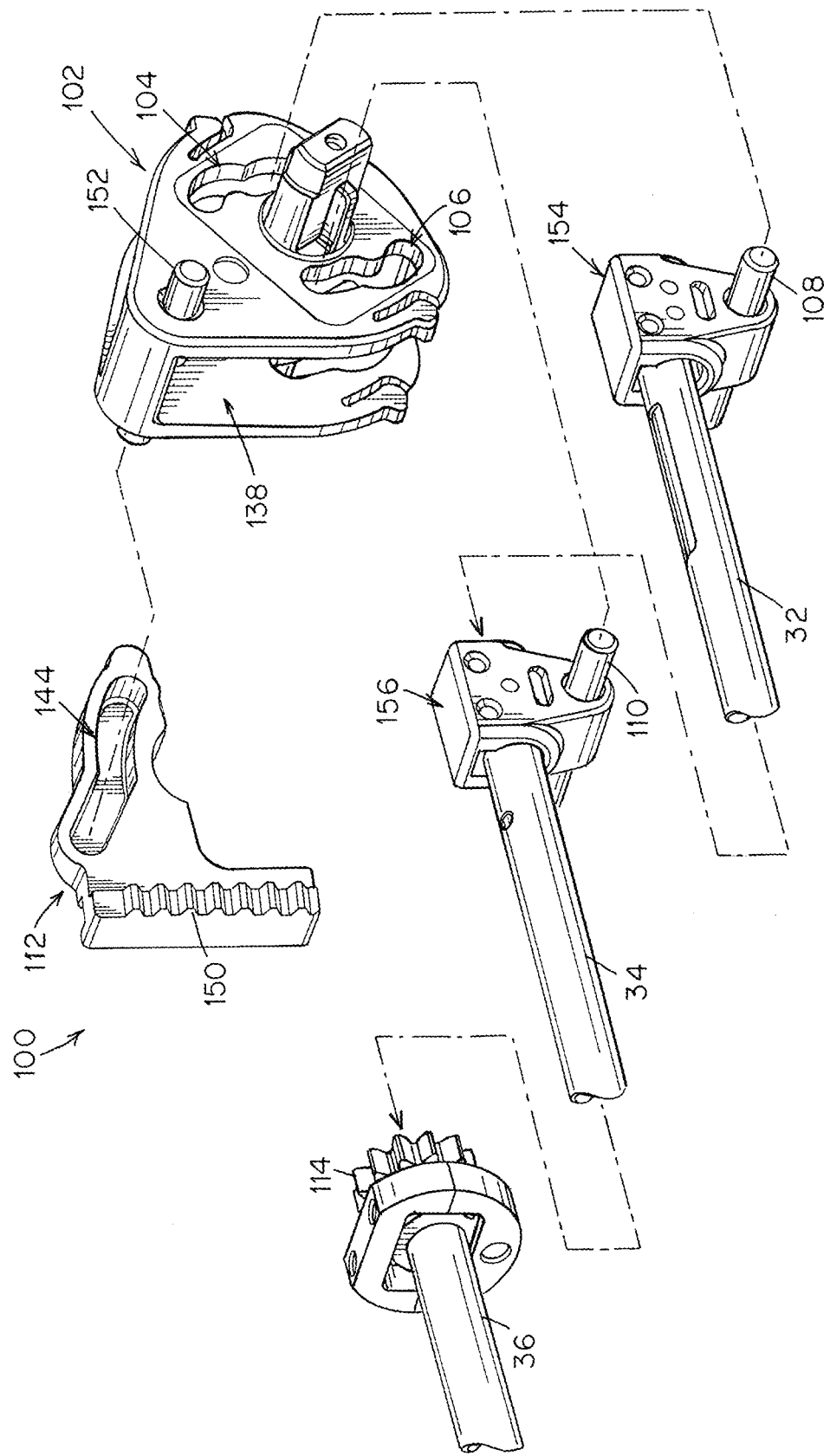

ARTICULATING SURGICAL INSTRUMENTS

CROSS-REFERENCES TO RELATED APPLICATIONS

This Application is a Division of U.S. application Ser. No. 15/867,035, filed Jan. 10, 2018, the disclosure of which is incorporated herein in its entirety.

FIELD

Disclosed embodiments are related to articulating surgical instruments.

BACKGROUND

A surgical mesh fabric or other prosthetic repair fabric may be used to surgically repair a hernia. The prosthetic repair fabric is typically placed in an open procedure or laparoscopically. Oftentimes a surgical instrument is used to secure the repair fabric in place by deploying one or more fasteners from a distal end of the surgical instrument through the prosthetic repair fabric and into the underlying tissue. However, a surgical instrument that includes a rigid elongated shaft assembly for deploying the fasteners may have a limited range of motion within the surgical field. Consequently, many surgical instruments include at least one articulable portion along the elongated shaft assembly to facilitate the orientation and placement of fasteners within the surgical field.

SUMMARY

In one embodiment, a surgical instrument includes a handle and an elongated shaft assembly extending distally from the handle. The elongated shaft assembly includes an articulable portion movable between a non-articulated configuration and an articulated configuration. The elongated shaft assembly includes a first articulating shaft and a second articulating shaft coaxially arranged relative to the first articulating shaft and axially fixed relative to the first articulating shaft at a location located distally from the articulable portion of the elongated shaft assembly. A proximal portion of the first articulating shaft is displaceable in a distal direction and a proximal portion of the second articulating shaft is displaceable in a proximal direction to move the articulable portion of the elongated shaft assembly from the non-articulated configuration to the articulated configuration.

In another embodiment, a method of operating a surgical instrument includes displacing a proximal portion of a first articulating shaft of an elongated shaft assembly of a surgical instrument in a proximal direction. The elongated shaft assembly includes an articulable portion movable between a non-articulated configuration and an articulated configuration. The method also includes displacing a proximal portion of a second articulating shaft of the elongated shaft assembly in a distal direction. The second articulating shaft is coaxially arranged relative to the first articulating shaft and axially fixed relative to the first articulating shaft at location located distally from an articulable portion of the elongated shaft assembly. The method further includes articulating the elongated shaft assembly from the non-articulated configuration to the articulated configuration, at least in part, due to the displacement of the proximal portion of the first articulating shaft and the proximal portion of the second articulating shaft.

In a further embodiment, a surgical instrument includes a handle and an articulation cam that is movable relative to the handle between at least a first position and a second position. The articulation cam includes a first cam profile and a second cam profile. The surgical instrument further includes an elongated shaft assembly extending distally from the handle, and the elongated shaft assembly includes a first shaft including a proximal portion coupled to the first cam profile and a second shaft including a proximal portion coupled to the second cam profile, the second shaft coaxially arranged relative to the first shaft. Moving the articulation cam from the first position to the second position displaces the proximal portion of the first shaft in a first direction and the proximal portion of the second shaft in a second direction.

In yet another embodiment, a method of operating a surgical instrument includes moving an articulation cam from a first position to a second position relative to a handle of a surgical instrument. The surgical instrument includes an elongated shaft assembly extending distally from the handle. The elongated shaft assembly includes a first shaft and a second shaft coaxially arranged relative to the first shaft. The articulation cam includes a first cam profile coupled to a proximal portion of the first shaft and a second cam profile coupled to a proximal portion of the second shaft. The method further includes displacing the proximal portion of the first shaft in a first direction, at least in part, due to movement of the articulation cam from the first position to the second position, and displacing the proximal portion of the second shaft in a second direction opposite the first direction, at least in part, due to movement of the articulation cam from the first position to the second position.

In another embodiment, a surgical instrument includes a handle and an elongated shaft assembly extending distally from the handle. The elongated shaft assembly includes an articulable portion movable between a non-articulated position and an articulated position. The surgical instrument further includes an articulation lock that selectively prevents articulation of the articulable portion of the elongated shaft assembly when the articulation lock is in a first locked configuration and permits articulation of the articulable portion of the elongated shaft assembly when the articulation lock is in a second unlocked configuration. The surgical instrument also includes an articulation control that controls articulation of the articulable portion of the elongated shaft assembly. Moving the articulation control from a first position to a second position moves the articulation lock from the first locked configuration to the second unlocked configuration to permit articulation of the articulable portion of the elongated shaft assembly, and moving the articulation control from the second position to a third position articulates the articulable portion of the elongated shaft assembly from the non-articulated position to the articulated position.

In a still further embodiment, a method of operating a surgical instrument includes moving an articulation control of a surgical instrument from a first position to a second position. The surgical instrument includes an elongated shaft assembly extending distally from a handle, and the elongated shaft assembly includes an articulable portion movable between a non-articulated position and an articulated position. The method further includes moving an articulation lock of the surgical instrument from a first locked configuration to a second unlocked configuration during movement of the articulation control from the first position to the second position. The articulation lock selectively prevents articulation of an articulable portion when the articulation lock is in the first locked configuration, and the articulation lock permits articulation of the articulable portion when the articulation lock is in the second unlocked configuration. The method also includes moving the articulation control from the second position to a third position, and articulating the articulable portion of the elongated shaft assembly from the non-articulated position to the articulated position during movement of the articulation control from the second position to the third position.

In another embodiment, a surgical instrument includes a handle and an elongated shaft assembly extending distally from the handle. The elongated shaft assembly includes an articulable portion movable between a non-articulated configuration and an articulated configuration. The elongated shaft assembly includes a first shaft including an articulable portion having a first plurality of cuts spaced along a first length of at least a distal portion of the first shaft. Each cut of the first plurality of cuts extends partially around a circumference of the first shaft to define a first spine extending along the first length of the first shaft, and the first spine has a first width at a distal end of the first spine and a second width greater than the first width at a proximal end of the first spine. The elongated shaft assembly further includes a second shaft coaxially arranged relative to the first shaft, and the second shaft includes an articulable portion having a second plurality of cuts spaced along a second length of at least a distal portion of the second shaft. Each cut of the second plurality of cuts extends partially around a circumference of the second shaft to define a second spine extending along the second length of the second shaft, and the second spine has a third width at a distal end of the second spine and a fourth width greater than the third width at a proximal end of the fourth spine. The first spine is located on a first side of the elongated shaft assembly, and the second spine is located on a second, opposing side of the elongated shaft assembly.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings:

FIG. 10 is an exploded view of a portion of the articulation control system of FIG. 6;

DETAILED DESCRIPTION

Figure 1:
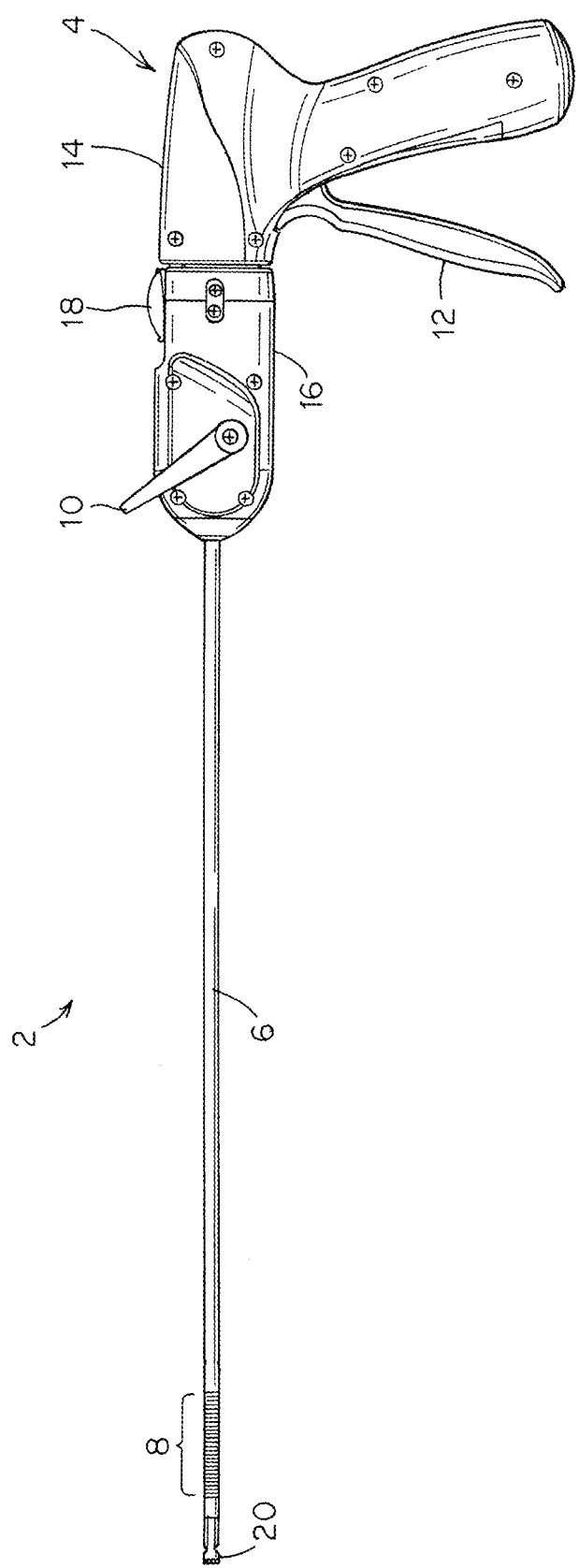
FIG. 1 is a schematic representation of one embodiment of an articulable surgical instrument.

The inventors have appreciated numerous benefits associated with surgical instruments that include an elongated shaft assembly having an articulable portion to allow at least a portion of the surgical instrument to be placed in one or more desired configurations and/or orientations. For example, articulation of the articulable portion may allow a distal tip of the elongated shaft assembly to be easily placed at desired position(s) and/or orientation(s) for performing a surgical procedure, such as deploying a surgical fastener into tissue. In some instances, it may be desirable to selectively permit or prevent articulation of the elongated shaft assembly with an articulation lock. For example, it may be desirable to prevent articulation during insertion and extraction of the surgical instrument into a surgical field, as may occur during laparoscopic surgery, and/or when it is desired to deploy fasteners in an unarticulated configuration. Thus, in some embodiments, the inventors have recognized that it may be desirable to provide a single integrated articulation control to allow a user to both selectively lock and unlock the articulation lock and control articulation of the articulable portion. Such an integrated articulation control may eliminate the use of a separate control for the articulation lock which may avoid adding additional steps and complexity to the typical operation of such a surgical device.

In some embodiments, the inventors have also appreciated benefits associated with articulable surgical instruments in which axial movement of a distal tip of an articulable shaft assembly is minimized when an articulable portion of the articulable shaft assembly is moved between a non-articulated configuration and an articulated configuration. For instance, maintaining an axial position of the distal tip during articulation may aid with accurate placement of the tip when deploying a fastener or performing another suitable surgical procedure.

Additionally, in yet other embodiments, the inventors have recognized that it may be desirable to provide an articulable elongated shaft assembly with sufficient rigidity to avoid excessive deflection of the elongated shaft assembly during actuation of the device when the elongated shaft assembly is in an articulated configuration. Such rigidity may help to maintain a distal tip of the elongated shaft assembly in a desired position and/or orientation during a surgical procedure and/or avoid excessive deflection of the shaft assembly when a force is applied to the distal tip. For example, the distal tip may be pressed into contact with a surface when deploying a fastener into tissue, and the rigidity of the elongated shaft assembly may limit the deflection of the tip to be less than a desired threshold deflection for a predetermined force applied to the distal tip.

As used herein, the term "distal direction" within a surgical device may refer to a direction that extends along a central longitudinal axis of the surgical device towards a distal end of the surgical device where a desired operation is performed. Correspondingly, a "proximal direction" may refer to a direction that is directed in an opposite direction relative to the distal direction such that it may be directed along the central longitudinal axis of the surgical device away from the surgical device's distal end where the desired operation is performed.

According to some embodiments, an elongated shaft assembly extends distally from a handle of a surgical instrument. The elongated shaft assembly includes an articulable portion that may articulate in at least one direction between a first position, which may correspond to a non-articulated configuration, to a second position, which may correspond to a fully articulated configuration in which the distal tip is oriented at an angle (e.g., an articulation angle) relative to a portion of the elongated shaft assembly located proximal to the articulable portion. When in the non-articulated, or straight configuration, a longitudinal axis passing through the articulable portion may be aligned with a longitudinal axis of the proximal portion of the elongated shaft assembly. Correspondingly, when in the fully articulated configuration, the distal tip of the elongated shaft assembly, and the longitudinal axis of the articulable portion, is oriented at an articulation angle relative to the longitudinal axis of the proximal portion. In one embodiment, the articulation angle of the fully articulated configuration may be between −30 degrees and 30 degrees, between −45 degrees and 45 degrees, between −90 degrees and 90 degrees, between −180 degrees and 180 degrees, between 15 degrees and 90 degrees, or between 45 degrees and 90 degrees, though it should be understood that the current disclosure is not limited to any particular range of articulation angles. Moreover, in some embodiments, the articulable portion may be movable to one or more additional articulated positions between the non-articulated (i.e., straight) configuration and the fully articulated configuration.

The surgical devices described herein may be made out of any desirable material or combination of materials. In some instances, the surgical devices described herein may be made from materials that are either sterilized and/or are sterilizable using any appropriate method including, but not limited to, heat, radiation, and/or pressure. Moreover, the materials may be capable of either being sterilized before, during, or after assembly and packaging to maintain sterility.

In one embodiment, a surgical instrument may include an elongated shaft assembly including a first articulating shaft and a second articulating shaft coaxially arranged relative to the first articulating shaft. The first and second articulating shafts may include flexible portions that form an articulable portion of the elongated shaft assembly, and the first and second articulating shafts are axially fixed relative to one another at a location distally located relative to the articulable portion. Proximal portions of the first and second articulating shafts may be displaceable relative to one another to move the articulable portion of the elongated shaft assembly between the first and second positions. For example, the proximal portions of the first and second articulating shafts may be displaced relative to one another to selectively place the first and second articulating shafts in opposing states of tension and/or compression. As discussed in more detail below, such tensile and/or compressive forces may be transmitted through a suitable structure in the articulable portion to apply and/or release a bending moment in the first and second articulating shafts, thereby moving the articulable portion between the non-articulated and articulated configurations. In some embodiments, the bending moment causes the articulable portion to move from the non-articulated configuration, which may correspond to a relaxed configuration of the elongated shaft assembly, to the articulated configuration. However, it should be understood that the current disclosure is not limited to embodiments in which a bending moment causes movement towards an articulated configuration. For example, in some embodiments, the fully articulated configuration may correspond to a relaxed (i.e., stress-free) state for the elongated shaft assembly, and application of a bending moment (or other suitable stresses) may cause the elongated shaft assembly to move toward the non-articulated (i.e., straight) configuration.

According to some aspects of the current disclosure, undesirable movement of a distal tip of an elongated shaft assembly may be reduced by displacing first and second articulating shafts of the elongated shaft assembly in opposing directions to move an articulable portion of the elongated shaft assembly between a non-articulated configuration and an articulated configuration. As discussed above, the first and second articulating shafts may be axially fixed at a location located distally relative to the articulable portion, and such opposing displacements of the proximal portions of the first and second articulating shafts may give rise to opposing tensile and compressive forces in the articulating shafts when moving the articulable portion between the non-articulated and articulated configurations. Without wishing to be bound by theory, these opposing displacements of the shafts may help to reduce axial displacement of the distal tip in excess of that expected from simply articulating the elongated shaft assembly.

In one embodiment, a surgical instrument may include an articulation control operable by a user to selectively move an articulable portion of an elongated shaft assembly of the device between non-articulated and fully articulated configurations. Additionally, the surgical instrument may include an articulation lock that is movable between a first locked configuration, in which the articulation lock prevents articulation of the articulable portion, and a second unlocked configuration, in which the articulation lock permits articulation. In some embodiments, the articulation control also may be associated with the articulation lock such that movement of the articulation control moves the articulation lock between the locked and unlocked positions. For example, in one embodiment, the articulation control may be movable from a first position, which may correspond to the articulable portion being in the non-articulated configuration and the articulation lock being in the locked configuration, to a second position corresponding to the articulation lock being moved to the unlocked position and the articulable portion remaining in the non-articulated configuration. The articulation control may be further movable from the second position to the third position, corresponding to the articulable portion being fully articulated. In this manner, a single articulation control may be used for both unlocking articulation of the articulable portion as well as for controlling the articulation Although embodiments described herein may include a single articulation control that controls both articulation of an articulable portion of an elongated shaft assembly and movement of an articulation lock, it should be understood that other arrangements may be suitable. For example, in some embodiments, a surgical instrument may include a separate lock control for moving the articulation lock between the locked and unlocked positions. Accordingly, it should be understood that the current disclosure is not limited to any particular arrangement of articulation and/or lock controls to move an articulable portion of an elongated shaft assembly and/or articulation lock.

Depending on the embodiment, an articulable portion of an elongated shaft assembly may be formed by one or more flexible portions of the associated shafts that permit articulation. For example, the flexible portions of the shafts may include a plurality of cuts extending in a transverse direction across a width of the shafts and arranged along at least a portion of the length of the various shafts comprising the elongated shaft assembly to provide a desired flexibility. In some embodiments, the cuts may define a preferential bending direction for the articulable portion, and articulating the articulable portion may involve bending the articulable portion along the preferential bending direction. Although articulable portions including cuts are described herein, other structures to permit articulation are also contemplated. For example, the articulable portion may include one or more weakened sections arranged to create a desired flexibility and/or preferred bending direction, interconnected flexible segments, interconnected segments connected by hinges, one or more flexible shafts, or any other suitable structure, as the disclosure is not limited in this regard.

As discussed above, it may be beneficial to provide a desired rigidity of the elongated shaft assembly while still permitting articulation of an articulable portion of the elongated shaft assembly. Accordingly, in some embodiments, the specific dimension and arrangement of the cuts, spines, and/or other suitable features of at least first and second articulating shafts of the elongated shaft assembly may be selected to provide the desired stiffness. In one embodiment, the first and second spines may have a tapered configuration with distal portions of the first and second spines being narrower than proximal portions thereof. This may provide an increased bending stiffness of the elongated shaft assembly at a proximal end of the spines and increased flexibility of the assembly at the distal end. Such a configuration may permit the distal end of the articulating shaft assembly to have enough flexibility to articulate to a desired articulated position while also becoming progressively stiffer at the proximal end of the articulable portion. Without wishing to be bound by theory, such a configuration may help to avoid undesired deflection of an elongated shaft assembly during use, for instance, when a user presses a distal end of the shaft assembly against a surface to deploy a fastener into tissue.

In addition to the above, the inventors have recognized that the number, size, and/or spacing of the cuts in the shafts of an articulable portion of an elongated shaft assembly may influence the resulting stiffness of the elongated shaft assembly in the non-articulated and/or articulated configurations. For example, the inventors have found that articulating shafts having increased numbers of cuts and smaller cut sizes in the articulable portion may provide for enhanced stiffness while still permitting a desired amount of articulation of the articulable portion. Accordingly, in some embodiments the number of cuts, the cut size, and/or cut spacing may be selected to provide a desired stiffness for the elongated shaft assembly. Specific sizings and spacings of the cuts are discussed in more detail below in regards to specific embodiments. Moreover, in some embodiments, at least a portion of the cuts may include stress reliefs at opposing ends of each cut to help reduce stress concentrations along the cuts. The stress reliefs may have any suitable shape including, for example, elliptical, circular, or any other appropriate shape.

As noted above, an elongated shaft assembly may include first and second articulating shafts that are placed in opposing states of tension and compression when an articulable portion of the elongated shaft assembly is in an articulated configuration. In some embodiments, the articulating shaft that is placed in the compressive state may include a plurality of cuts that are sized and shaped such that opposing sides of each of the cuts come into contact with one another when the articulable portion is fully articulated. For example, the inventors have appreciated that such configurations may impart additional stability and/or rigidity to a distal portion of the elongated shaft assembly when in the articulated configuration.

For the sake of clarity, the currently disclosed embodiments discussed below in regards to the figures are directed to a laparoscopic device for deploying one or more fasteners. However, the current disclosure is not limited to laparoscopic devices for deploying one or more fasteners. Instead, the disclosed articulation systems, locking mechanisms, controls, and surgical fasteners may be used in any appropriate surgical instrument including an articulable portion. For example, appropriate surgical instruments may include an endoscopic device, a borescopic device, a catheter, a surgical instrument for use in "open" procedures, or any other appropriate surgical instrument. Further, the disclosed surgical instruments may include any appropriate end effector and are not limited to the deployment of fasteners. However, in those embodiments including fasteners, the instrument including the articulation locking mechanism may be loaded with one or more fasteners, or it may be constructed to allow the user to load the instrument with one or more fasteners. In addition, disclosed embodiments that include fasteners are described with regards to a generic fastener. Consequently, it should also be understood that any appropriate fastener might be used with the currently disclosed articulation locking mechanisms including a tack, a clip, a staple, a pin, a tissue anchor, a bone anchor, or any other appropriate type of fastener.

Turning to the figures, specific non-limiting embodiments are described in further detail. It should be understood that the various systems, components, features, and methods described relative to these embodiments may be used either individually and/or in any desired combination as the disclosure is not limited to only the specific embodiments described herein.

FIG. 1 depicts one embodiment of a surgical instrument 2. The surgical instrument includes a handle 4 and an elongated shaft assembly 6 extending distally from the handle toward a distal end 20, from which fasteners may be deployed. The elongated shaft assembly 6 includes an articulable portion 8 that is moveable between a non-articulated (i.e., straight) position, and one or more articulated (i.e., curved or bent) positions. Articulation of the articulable portion 8 may be controlled by an articulation control 10, such as a rotatable and/or axially displaceable knob, handle, lever, or other feature which may be moved relative to the handle 4 between one or more positions to move the articulable portion 8 between the non-articulated configuration and the one or more articulated configurations. The surgical instrument 2 also includes a trigger 12 for actuating a fastener deployment system to deploy a fastener, though other appropriate types of actuation systems to perform other types of operations are also contemplated.

The articulable portion 8 of the elongated shaft assembly may be moved between at least a first position, such as an unarticulated (i.e. straight) position, and second position, such as a fully articulated position, using the articulation control 10. Depending on the embodiment, the articulable portion 8 may be moved to one or more preselected articulation angles, or the articulable portion 8 may be adjusted to one or more arbitrary (i.e. not preselected) articulation angles. The articulable portion 8 may be articulated in at least a first direction, though embodiments in which the articulable portion articulates in at least a second direction are also envisioned. For example, the articulable portion 8 may be articulated in a first direction corresponding to an articulation angle greater than approximately 0° and in an opposing second direction corresponding to an articulation angle less than approximately 0°. Alternatively, or in addition to the above, the articulable portion 8 might be articulated about two different axes (e.g. articulation in the horizontal direction and the vertical direction) such that it articulates in at least two directions.

In some embodiments, it may be desirable to rotate the elongated shaft assembly 6 to facilitate positioning of the distal tip. For example, the elongated shaft assembly 6 may simply be adapted to be rotatable relative to at least a portion of the handle 4. Alternatively, a portion of the handle 4 including the elongated shaft assembly 6 may be rotatable relative to another portion of the handle 4, such as the portion including the grip. One such embodiment is depicted in FIG. 1. In the depicted embodiment, the surgical instrument 2 includes a first handle portion 14 and a second handle portion 16 from which the elongated shaft assembly 6 extends. The first and second handle portions 14 and 16 may be constructed and arranged in any appropriate fashion to be rotatable relative to one another. The surgical instrument may include a rotation lock 18 that is movable to selectively permit and prevent rotation of the second handle portion 16 relative to the first handle portion 14. It should be understood that while a surgical instrument including a rotatable elongated shaft assembly 6 or handle 4 is depicted in the figures, a surgical instrument including a unitary handle and/or an elongated shaft assembly 6 that is stationary relative to the handle are also possible as the current disclosure is not limited in this manner.

In certain applications, it may be advantageous to include a distal rigid straight portion 20 that is distally located from the articulable portion 8 of the elongated shaft assembly. The rigid straight portion 20 may include a number of features to aid in the deployment of fasteners from the distal end of the elongated shaft assembly 6. For example, the distal rigid straight portion 20 may include fastener retaining elements such as tabs to retain a distal most fastener in a fastener deployment position prior to actuation of the surgical instrument. Additionally, without wishing to be bound by theory, when a driveshaft of a fastener deployment system applies a force to a fastener as it goes around an articulated portion of the elongated shaft assembly, the force applied by the drive shaft to the head of the fastener may not be fully aligned with the deployment direction of the associated fastener. For example, a distal-most fastener may be located distally relative to a distal end of the driveshaft, and correspondingly, the fastener may be located within a portion of the elongated shaft assembly that is oriented at an angle that is larger than a portion of the elongated shaft assembly containing the distal end of the drive shaft. Consequently, when the drive shaft applies a force to the fastener (e.g., via reciprocal movement of the driveshaft), the force applied to the fastener may be misaligned with a longitudinal axis of the fastener.

Figure 3:
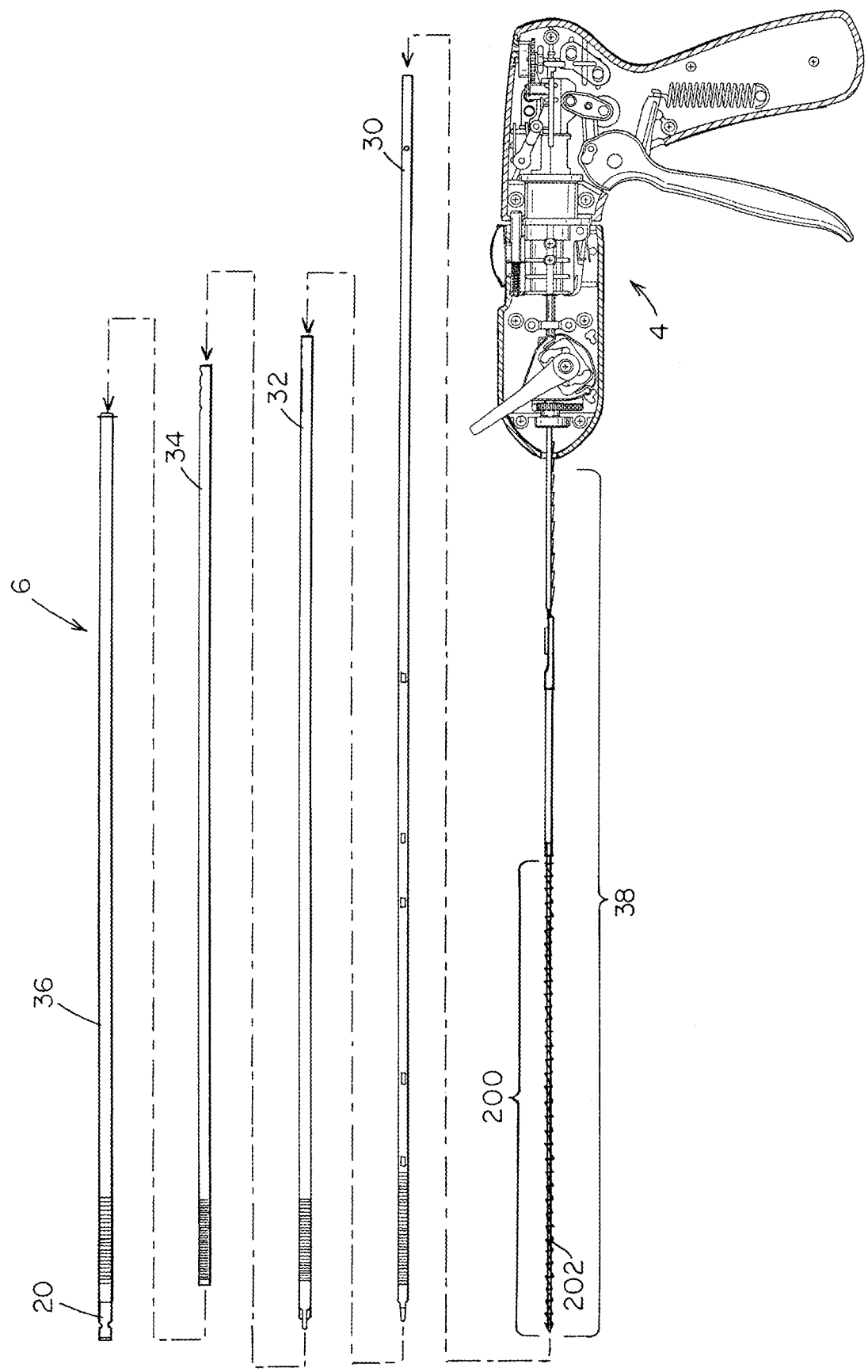
FIG. 3 is an exploded view of the elongated shaft assembly of the surgical instrument of FIG. 1.

In view of the foregoing, it may be desirable to include the distal rigid straight portion 20 to provide a straight portion of the elongated shaft assembly with a sufficient length to accommodate a fastener and to permit the actuation force from the fastener deployment system to be applied to that fastener in the same direction as the fastener deployment direction. Without wishing to be bound by theory, this may result in reduced actuation forces required to deploy a fastener from the surgical instrument. In some embodiments, the length of the distal rigid straight portion may be equal to or greater than a length of a fastener such that the distal end of the driveshaft may be aligned in the deployment direction. For example, as illustrated in FIG. 3, the distal rigid straight portion 20 is longer than the length of the fasteners 202. In this manner, both a distal-most fastener and the distal end of the driveshaft may be received in the distal rigid straight portion to aid in aligning the deployment force from the driveshaft with the orientation of the fastener. While a surgical instrument 2 including a distal rigid straight portion 20 has been described herein, and depicted in the figures, it should also be understood that embodiments are envisioned in which the articulable portion 8 extends all the way to the distal end of the elongated shaft assembly 6 such that the surgical instrument does not include a distal rigid straight portion.

Figure 2:
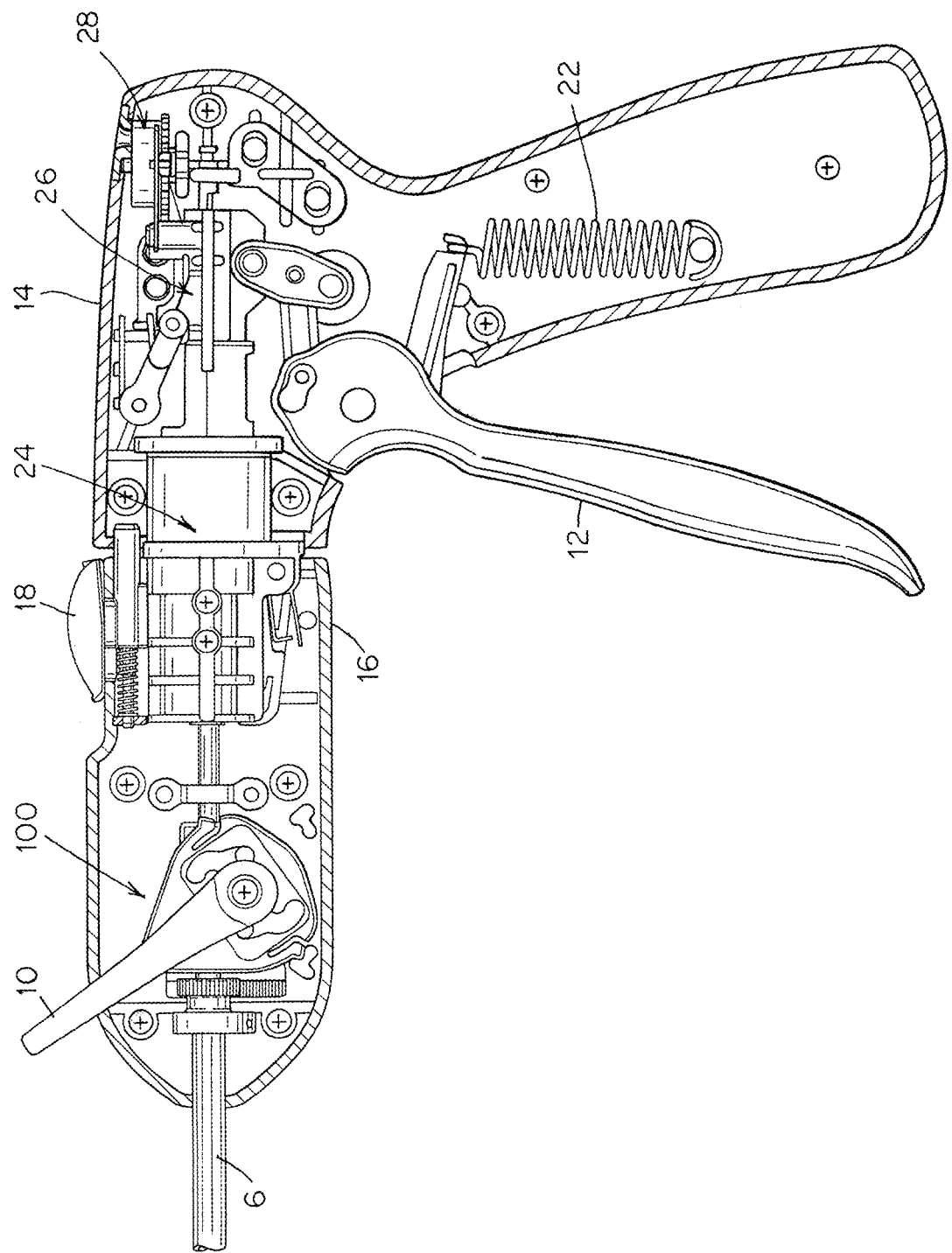
FIG. 2 is a side view of an interior portion of the articulable surgical instrument of FIG. 1.

FIG. 2 is a schematic side view of the surgical instrument of FIG. 1, showing the various components and systems that may be provided within the handle 4. As illustrated, the trigger 12 may be coupled to a return spring 22, which may provide a restoring force to urge the trigger back towards an unactuated position following actuation of the trigger to deploy a fastener. The trigger may be coupled to a drive system 24 constructed and arranged to apply a deployment force to a fastener upon actuation of the trigger 12 to deploy the fastener from the distal end of the elongated shaft assembly 6. Moreover, in some embodiments, the surgical instrument may include an actuation lockout system 26 that may selectively prevent activation of the drive system 24 until a force applied to the trigger exceeds a threshold force. Although a specific drive system and actuation lockout system are shown in the figures, it should be understood that the current disclosure is not limited to surgical instruments including any particular drive systems and/or actuation lockout systems. For example, any appropriate arrangement of cams, linkages, gears, clutches, and other appropriate components may be used in any appropriate combination as part of a drive system.

In some embodiments, a surgical instrument may include a plurality of fasteners within the elongated shaft assembly 6, and the fasteners may be deployed sequentially upon subsequent actuations of the trigger 12. In some such embodiments, it may be desirable to monitor the number of fasteners remaining within the elongated shaft assembly that have not yet been deployed. Accordingly, the surgical instrument 2 may include a fastener level indicator system 28 that is constructed and arranged to provide an indication of the number of fasteners available for deployment. For example, the fastener level indicator system 28 may be coupled to the trigger 12 such that upon actuation of the trigger (and deployment of a fastener), the fastener level indicator system may move a corresponding indicator to indicate that the number of fasteners remaining has decreased by one (e.g., see FIGS. 21-23 detailed further below). However, it should be understood that other systems for monitoring the number of remaining fasteners also may be used, and that the surgical instrument may not include a fastener level monitoring system in some embodiments, as the disclosure is not limited in this regard.

In addition to the above, FIG. 2 depicts an articulation control system 100 according to some embodiments. As described in more detail below, the articulation control system is coupled to the articulation control 10 and one or more shafts of the elongated shaft assembly 6 such that moving the articulation control 10 applies a suitable articulation force to the one or more shafts, or other component of the elongated shaft assembly, to selectively move the articulable portion 8 of the elongated shaft assembly between at least an unarticulated and an articulated position.

FIG. 3 depicts an exploded view of the elongated shaft assembly 6 of the surgical instrument 2 which extends distally from the handle 4. The elongated shaft assembly includes a drive shaft 30, which may be driven by a suitable drive system (such as drive system 24 discussed above) to apply a distally directed force to a fastener to deploy the fastener from the distal end of the elongated shaft assembly. The elongated shaft assembly further includes a first articulating shaft 32, which may be an inner articulating shaft, a second articulating shaft 34, which may be an outer articulating shaft, and an articulation lock in the form of a locking shaft 36. As described in more detail below, the first and second articulating shafts are constructed and arranged to apply an articulation force to the elongated shaft assembly to move the articulable portion 8 between the non-articulated position and the one or more articulated positions.

As illustrated in FIG. 3, the various shafts of the elongated shaft assembly may be arranged coaxially relative to one another. For instance, in the depicted embodiment, the fastener carrier and follower assembly 38 is received within the driveshaft, which is received within the first and second articulating shafts 32, 34 and locking shaft 36. Although a particular arrangement of shafts is shown in the figures, it should be understood that other arrangements also may be suitable. For example, in one embodiment, the locking shaft 36 may be located within the first and second articulating shafts 32, 34. Accordingly, the current disclosure is not limited to any specific arrangement of shafts comprising the elongated shaft assembly.

In some embodiments, a fastener carrier and follower assembly 38 is provided within an elongated shaft assembly. For example, a stack 200 of fasteners may be slidably disposed on a fastener carrier. The follower may be located proximally relative to the fastener stack 200 and may apply a distally directed force to one or more surgical fasteners of the stack to urge the stack of fasteners in the distal direction. Appropriate types of followers include, but are not limited to, compressed springs, ratchet and pawl mechanisms, walking beam assemblies, and/or any other appropriate type of mechanism capable of moving the stack of fasteners in a distal direction toward a distal end of the device.

Figure 4:
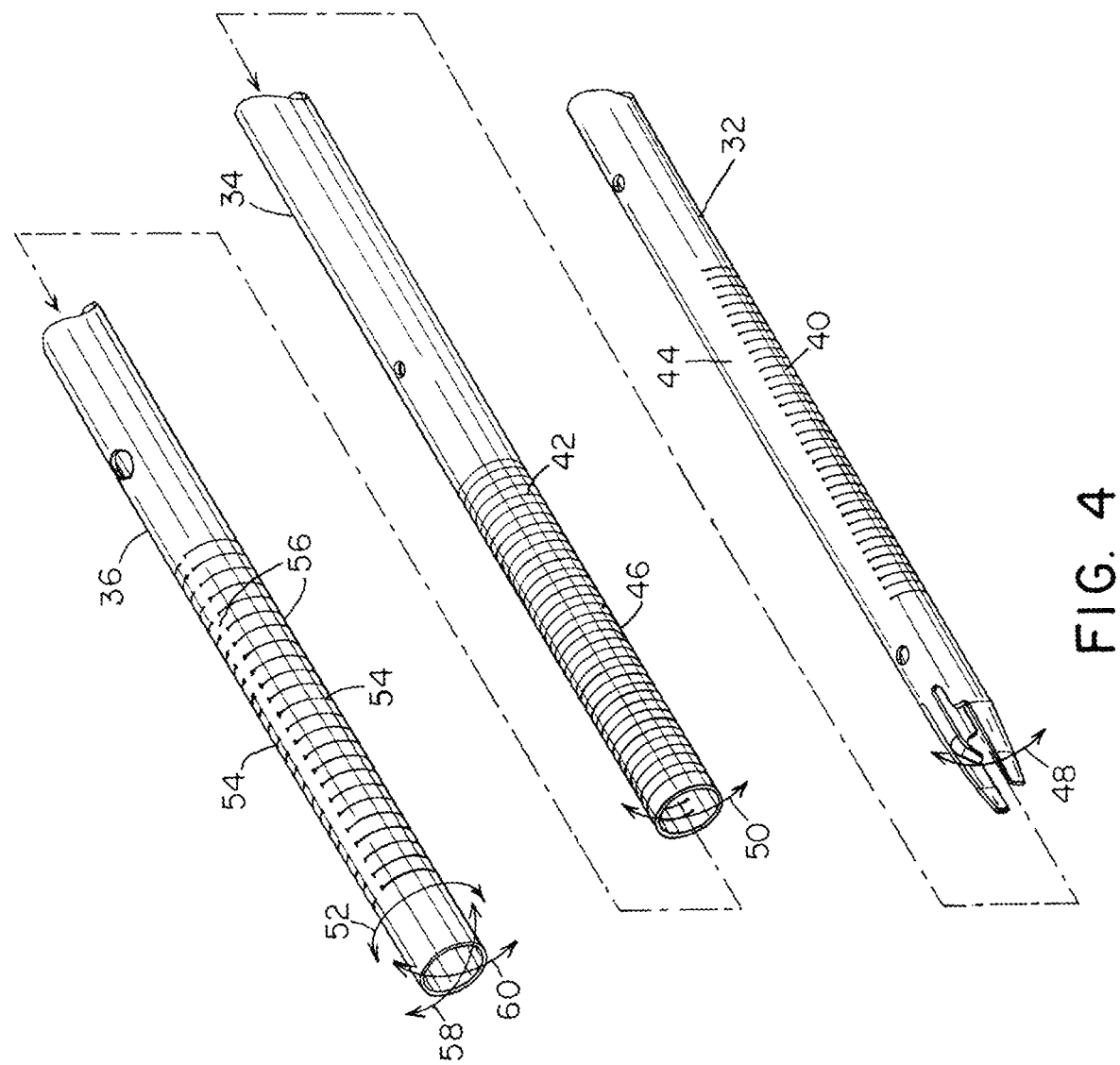
FIG. 4 is an exploded view of a portion of the elongated shaft assembly of FIG. 3.

FIG. 4 shows an exploded perspective view of a first articulating shaft 32, second articulating shaft 34, and locking shaft 36. Each of these shafts may include a flexible portion located in the articulable portion 8 of the elongated shaft assembly. As illustrated, the flexible portions include a plurality of cuts which define one or more spines extending along a length of the shafts in the articulable portion. In particular, the first articulating shaft 32 includes a first plurality of cuts 40 extending in a transverse direction partially around a circumference of the first articulation shaft and are spaced from one another along a length of the shaft to define a first spine 44 extending along a length of the flexible portion of the first articulating shaft. Similarly, the second articulating shaft 34 includes a second plurality of cuts 42 extending in a transverse direction partially around a circumference of the second articulation shaft and are spaced from one another along a length of the shaft to define a second spine 46. The cuts 40, 42 and spines 44, 46 may define respective preferential bending directions for the first and second articulating shafts 32 and 34 oriented in a direction that is perpendicular to a direction in which the spines extend. For example, the first articulating shaft 32 has a preferred bending direction 48 and the second articulating shaft 34 has a preferred bending direction 50. In the depicted embodiment, the bending directions 48 and 50 are parallel, but the first and second spines 44, 46 are located on opposing sides of the elongated shaft assembly. As discussed in more detail below, such a configuration may result in the first and second articulating shafts bending in the same direction when the first and second articulating shafts are placed in opposing states of tension and compression.

Depending on the particular embodiment, the first and second articulating shafts may include any suitable structure to provide desired preferential bending directions. For example, as discussed above, the first and second articulating shafts may include spines positioned opposite one another to define parallel preferential bending directions for the first and second articulating shafts. In some embodiments, the first and second spines may be parallel to a longitudinal axis of the elongated shaft assembly, though other configurations are also contemplated. For example, the first and second spines may extend helically around opposing sides the first and second articulating shafts, respectively. Accordingly, it should be understood that the first and second spines may be arranged in any suitable manner.

In addition to the cuts and spines on the articulating shafts, the locking shaft 36 may include two sets of cuts 54 which define opposing spines 56 extending along at least a portion of a length of the locking shaft and along a length of the flexible portion. In this manner, the cuts 54 and spines 56 define a preferential bending direction 58 that is perpendicular to a plane passing between the opposing spines as well as a direction of bending resistance 60 in a direction extending between the opposing spines. In some embodiments, the locking shaft 36 is rotatable in direction 52 about a longitudinal axis of the elongated shaft assembly and relative to the first and second articulating shafts 32, 34. For example, locking shaft may be rotated to an unlocked position in which the preferential bending direction 58 of the locking shaft is aligned with the preferential bending directions 48, 50 of the first and second articulating shafts to permit articulation of the articulable portion 8 of the elongated shaft assembly 6. Similarly, the locking shaft may be rotated to a locked position in which the direction of bending resistance 60 is aligned with the preferential bending directions of the articulating shafts to inhibit or prevent articulation. Moreover, and similar to the spines on the first and second articulating shafts, the spines 56 may be arranged in any suitable manner on the locking shaft, such as parallel to a longitudinal axis of the elongated shaft assembly, at an angle relative to the longitudinal axis, helically around opposing sides of the locking shaft, and so on.

While several possible embodiments including an articulation lock in the form of a locking shaft rotatable relative to first and second articulating shafts are described herein, other arrangements for the articulation lock are contemplated. For example, the articulation lock may include a locking shaft that is axially movable relative to the articulating shafts to move the locking shaft between locked and unlocked configurations. The locking shaft may include a flexible portion, and the axial movement may selectively align or overlap the flexible portion of the locking shaft with an articulable portion of an elongated shaft assembly to permit articulation. When the flexible portion is not aligned with the articulable portion, the locking shaft may inhibit articulation of the articulable portion. Accordingly, it should be understood that the current disclosure is not limited to any particular structures for an articulation lock to selectively permit and prevent articulation of the elongated shaft assembly.

Figure 5:
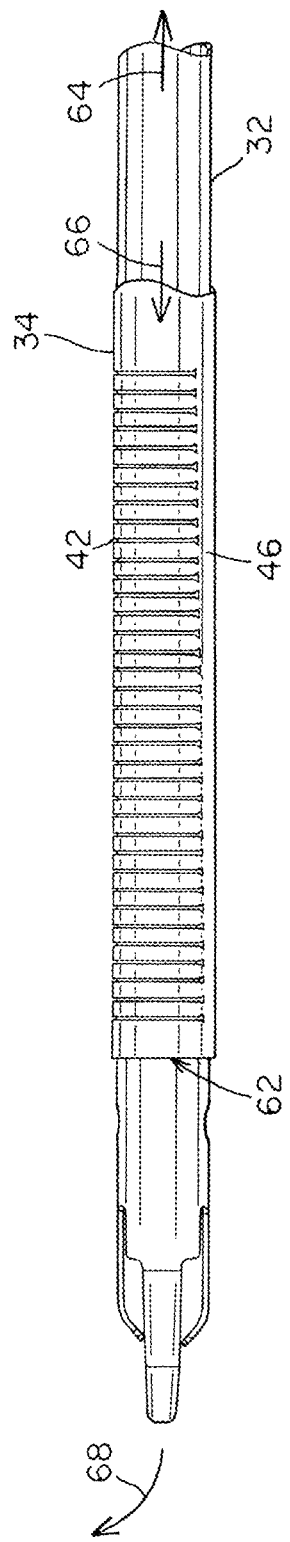
FIG. 5 is a side view of the first and second articulating shafts of the surgical instrument of FIG. 1.

As shown in FIG. 5, the first and second articulating shafts 32 and 34 may be attached to one another at an attachment point 62, which is located distally from the articulable portion of the elongated shaft assembly. This attachment may axially fix the first and second articulating shafts to one another at the attachment point. In the depicted embodiment, the attachment point is located at the distal end of the second articulating shaft 34, though other configurations also may be suitable. For example, the second articulating shaft may extend beyond the attachment point such that the attachment point is spaced from the distal end of the second articulating shaft. Moreover, it should be understood that the first and second articulating shafts may be attached in any suitable manner, such as with an adhesive, one or more fasteners, one or more pins, one or more welds, and/or any other appropriate form of connection.

Due to the attachment of the first and second articulating shafts 32, 34 at the distally located attachment point 62, application of axial forces and/or displacements to corresponding proximal portions of the first and second shafts may place the first and second shafts in a state of tension and/or compression. For example, a proximally directed force and displacement 64 applied to a proximal portion of the first articulating shaft 32 may create a tensile stress in the first articulating shaft. Similarly, application of a corresponding distally directed force and displacement to a proximal portion of the second articulating shaft 34 may create a compressive stress in the second articulating shaft. These opposing tensile and compressive stresses are transmitted through the opposing spines 44 and 46 of the first and second articulating shafts which are both offset from a neutral bending axis of the overall elongated shaft assembly. This creates a bending moment in the articulating shafts which causes the articulating shafts to bend along direction 68 to move the elongated shaft assembly toward an articulated position. It should be understood that the proximally and distally directed forces and displacements may be applied to the first and second shafts, respectively, via any suitable articulation control system, as discussed in more detail below.

Although a particular arrangement of forces and/or displacements applied to the first and second articulating shafts are shown in the figures and described above to move the elongated shaft assembly toward the articulated position, other arrangements also may be suitable. For example, in some embodiments, articulating the elongated shaft assembly may involve applying a distally directed force and/or displacement to the proximal portion of the first articulating shaft 32 and a proximally directed force and/or displacement to the proximal portion of the second articulating shaft 34 which would cause the elongated shaft assembly to articulate in the opposite direction to that shown in FIG. 5. Alternatively, in certain embodiments, the first and second articulating shafts may form an elongated shaft assembly with a resting shape (i.e., when no stresses are applied) that is curved (e.g., along a direction corresponding to an articulated configuration), and the first and second articulating shafts may be placed into opposing states of tension and compression to move the elongated shaft assembly to the non-articulated (i.e., straight) configuration. Accordingly, it should be understood that the currently disclosed articulating shaft assemblies are not limited with regards to what direction they articulate and/or the final configuration they are in when placed into a state of compression and/or tension.

While several possible embodiments related to the construction of the articulable elongated shaft assembly are described herein, it should be understood that the current disclosure is not limited to only the described embodiments. For example, the articulable portion of an elongated shaft assembly may be constructed and arranged in any appropriate fashion to provide articulation in a desired direction. Further, while a specific type of articulation mechanism using articulating shafts with opposing spines is described, other mechanisms for articulating an elongated shaft assembly may be suitable. For example the articulable portion of the elongated shaft assembly may be articulated using: one or more control wires, ribbons, or slats associated with the articulable portion; pre-stressed members and retractable sheaths, rigid linkages associated with pivot joints; or any other appropriate structure capable of articulating the articulable portion.

As discussed previously, a surgical instrument may include an articulation control to selectively move an articulable portion of an elongated shaft assembly between the non-articulated and articulated positions. Depending on the particular embodiment, the articulation control may be coupled to articulating shafts of the elongated shaft assembly via any suitable structure to control the articulation. Referring to FIGS. 6-14, embodiments of an articulation control system 100 are described in more detail.

Figure 6:
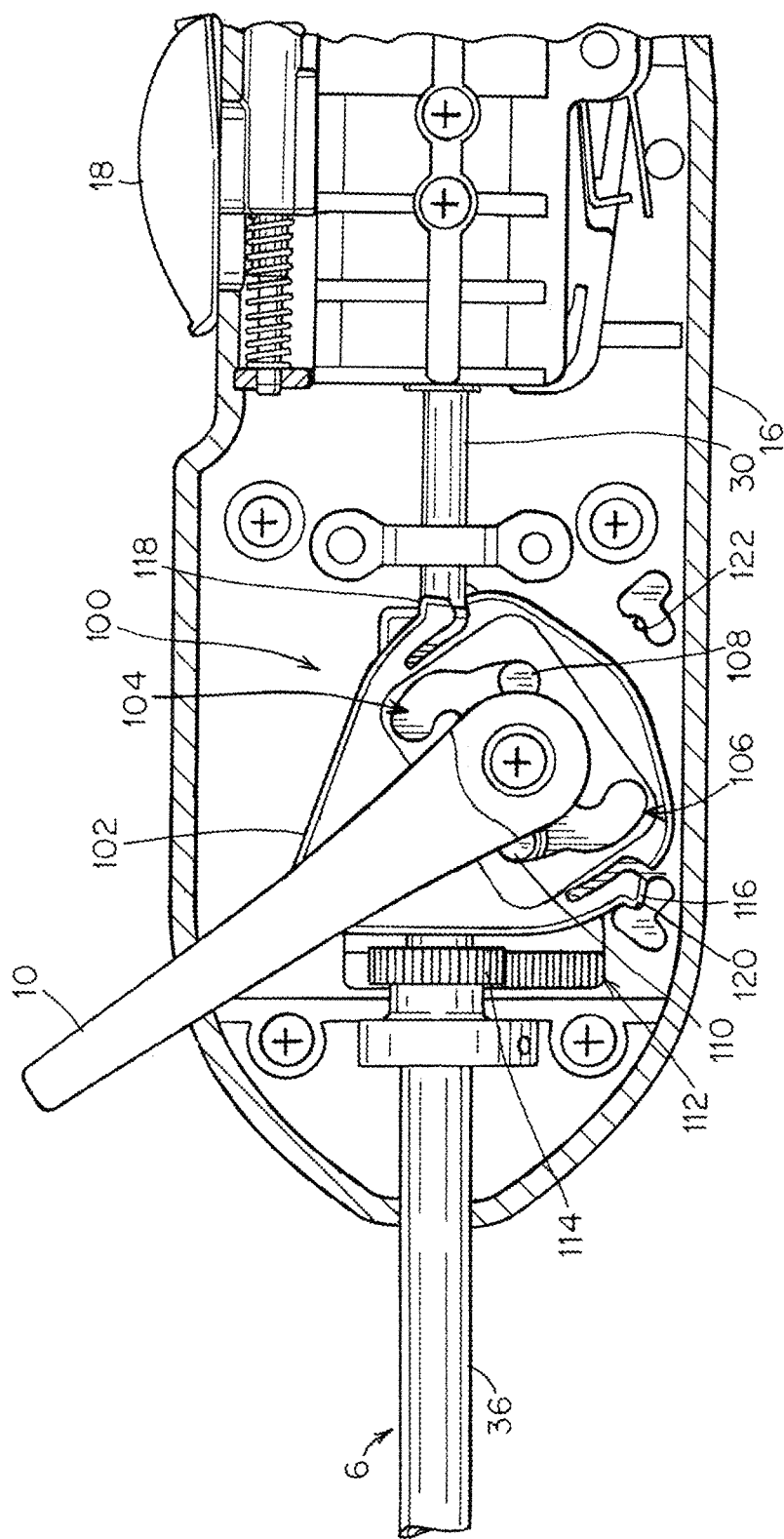
FIG. 6 is a close up side view of the surgical instrument of FIG. 1 including an articulation control system according to one embodiment, with the articulation control system in a first position.

FIG. 6 is a schematic side view of an articulation system 100 in a first position, which may correspond to the elongated shaft assembly being in the non-articulated (straight) configuration. The articulation system includes an articulation cam 102 that is coupled to the articulation control 10, such that movement of the articulation control 10 causes associated movement of the articulation cam 102. In the depicted embodiment, rotational movement of the articulation control causes the articulation cam to rotate relative to an associated portion of the handle including, for example, a rotatable handle portion 16 of the surgical instrument. While rotation has been illustrated, it should be understood that other types of movement including, for example, translational movement of the articulation control and articulation cam are also envisioned as the current disclosure is not limited to a rotatable articulation cam.

In the depicted embodiment, the articulation cam 102 includes first and second cam profiles 104 and 106 which may be located on opposing sides of a rotational axis of the cam. The cam profiles may be constructed and arranged to receive first and second articulation pins 108 and 110, respectively. The first and second articulation pins may be coupled to respective proximal portions of the first and second articulating shafts, such that movement of the articulation pins within the cam profiles displaces the proximal portions of the articulating shafts. For example, as discussed in more detail below, each of the cam profiles 104 and 106 may include one or more profile portions located at different radial distances from the rotational axis of the articulation cam 102. Consequently, rotation of the articulation cam may move the pins between the profile portions located at different radial distances to displace the associated proximal portions of the articulating shafts. While embodiments including articulation pins coupled to cam profiles are described herein, it should be understood that other structures to couple the articulating shafts to the articulation cam also may be suitable, as the current disclosure is not limited in this regard.

In addition to controlling articulation of the articulating shaft assembly, the articulation control system 100 may also be used to move an associated locking shaft 36 between locked and unlocked positions to selectively inhibit or permit articulation of the elongated shaft assembly. In the depicted embodiment, the articulation cam 102 is coupled to a locking cam 112, which is in turn coupled to the locking shaft 36 via a gear 114. As discussed in more detail below, movement of the articulation cam (e.g., rotational movement) may correspondingly displace the locking cam, which may rotate the gear 114. Rotation of gear 114 may then rotate the locking shaft 36 to move the locking shaft between locked and unlocked configurations as discussed previously above.

Figure 12:
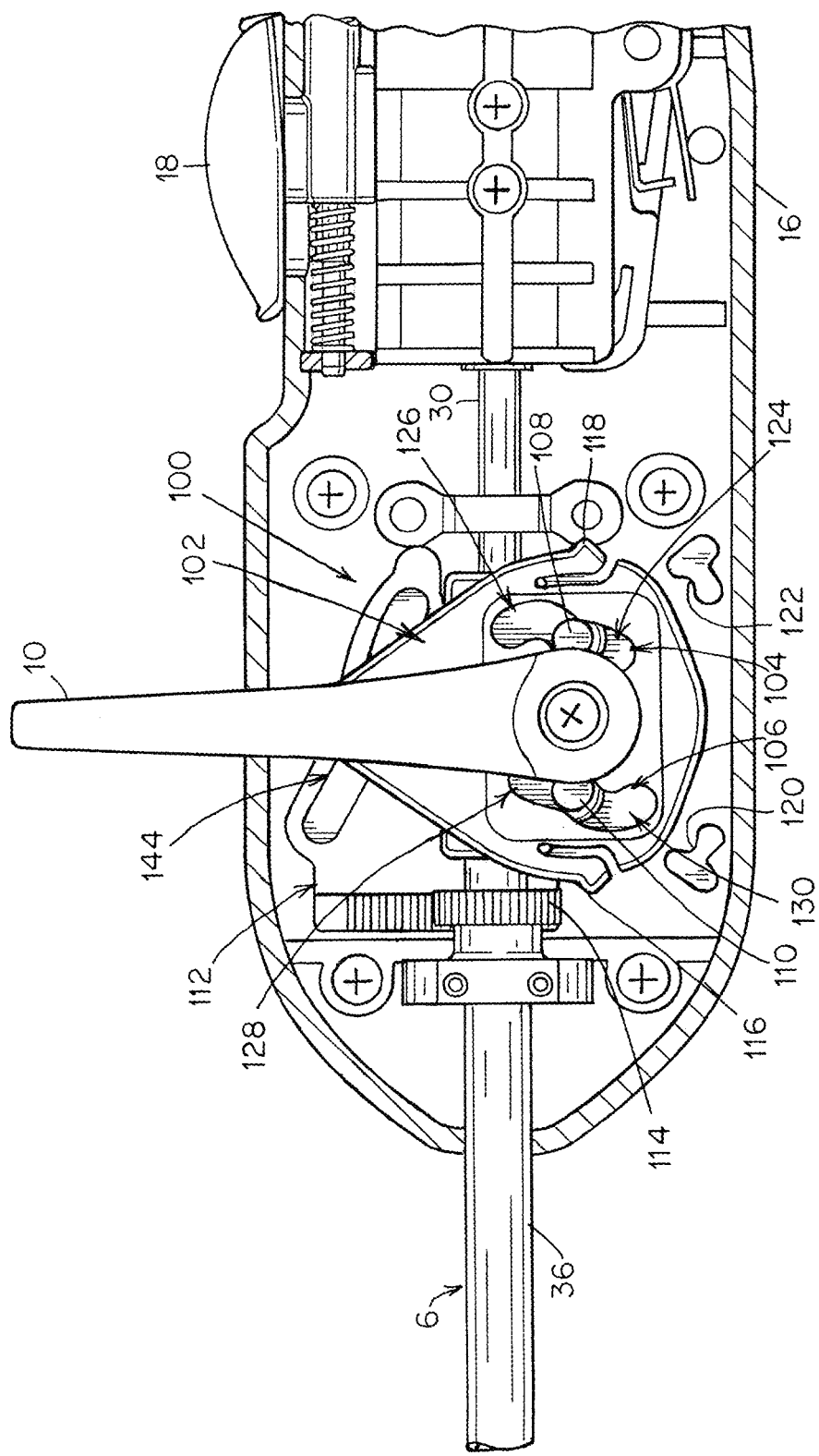
FIG. 12 is a side view of the articulation control system of FIG. 6 in a second position.

In some embodiments, it may be desirable for an articulation control system to include one or more features to aid in maintaining an elongated shaft assembly in the non-articulated position or in one or more articulated positions. For example, one or more detent mechanisms or other appropriate form of lock may help to avoid undesired movement of the articulation control system and/or undesired movement of the elongated shaft assembly toward or away from the articulated position. In the depicted embodiment, the articulation control system may include first and second cam locks 116 and 118 corresponding to resilient arms extending out from the articulation cam 102. Corresponding features, such as recesses 120 and 122, are provided on an interior surface of the rotatable handle portion 16, and engagement of the cam locks 116, 118 with the recesses 120, 122 may function as a detent mechanism to maintain the articulation cam 102 in a desired orientation. For example, as shown in FIG. 6, engagement of the first cam lock 116 with recess 120 maintains the articulation control system in the first position to maintain the elongated shaft assembly in the non-articulated position. Similarly, as shown in FIG. 12, engagement of the second cam lock 118 with the second recess 122 may aid in maintaining the elongated shaft assembly in the fully articulated position. When movement of the articulation control is desired, the resilient arms may deform to allow the cam locks to disengage from the corresponding recesses.

Although embodiments including two cam locks and two associated recesses corresponding to the non-articulated and fully articulated positions for the elongated shaft assembly have been depicted, it should be understood that the articulation control system may include any suitable number and/or type of cam locks. For instance, in some embodiments, one or more additional cam locks and recesses may be provided to maintain the articulation control system at one or more intermediate positions, which may correspond to a partially articulated position for the elongated shaft assembly. In other embodiments, the articulation control system may not include any cam locks. For instance, frictional engagement between the various components of the articulation control system may be sufficient to maintain the articulation control at a desired position, or the articulation control system may be held at a desired position via user input to the articulation control 10.

As discussed previously, in some embodiments, it may be desirable for an articulation control system to apply opposing displacements to proximal portions of first and second articulating shafts. For example, such opposing displacements may place the first and second articulating shafts in opposing states of tension and/or compression (e.g., due to the shafts being axially fixed at a distally located attachment point), which may reduce motion of a distal tip of the elongated shaft assembly during articulation of the articulable portion of the surgical instrument. Accordingly, the various cam profiles of the articulation cam may be shaped to provide this desired motion for the proximal portions of the articulating shafts, as discussed below.

Figure 7:
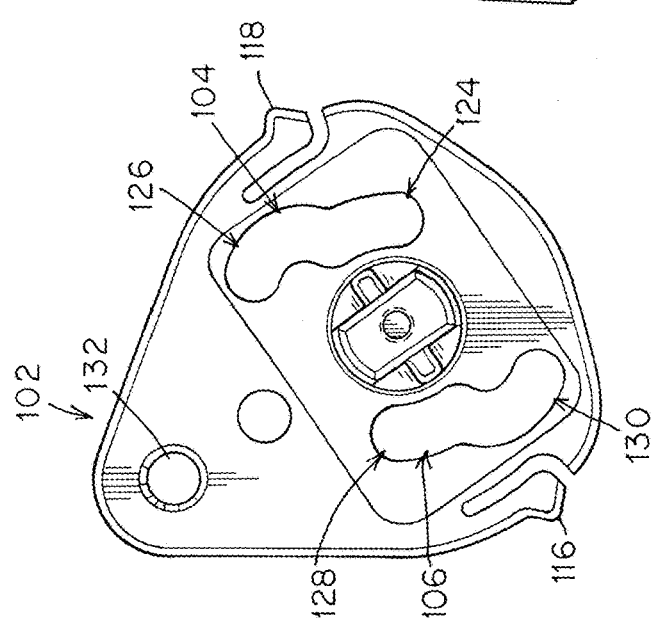
FIG. 7 is a side view of one embodiment of an articulation cam.

For example, FIG. 7 shows a schematic side view of the articulation cam 102 of the articulation control system 100. As illustrated, the first cam profile 104 includes a first profile portion 124 and a second profile portion 126. Similarly, the second cam profile 106 includes a third profile portion 128 and a fourth profile portion 130. The first and third profile portions follow curved paths, which may be at constant radial distances from a rotational axis of the articulation cam. In some embodiments, the first and third profile portions may be located at a constant first radial distance from the rotational axis. Correspondingly, the second and fourth profile portions follow curved paths located at radial distances different from the radial distance of the corresponding first and third profile portions. For example, the second and fourth profile portions may extend to a second larger radial distance from the rotational axis. In this manner, when the first and second articulation pins 108 and 110 associated with proximal portions of first and second articulating shafts (not shown in FIG. 7) are moved within the first and second cam profiles 104 and 106, respectively, the articulation pins are displaced relative to the rotational axis of the articulation cam. Since the articulation pins and articulating shafts are constrained to moving in the axial direction, this results in axial displacement of the pins and shafts towards and/or away from a rotational axis of the articulation cam depending on the direction of rotation.

While embodiments are described herein in which an articulation cam includes cam profiles with multiple profile portions, it should be understood that the disclosure is not limited in this manner, and that the cam profiles may have any suitable configuration such that the cam profiles cause a desired movement of the proximal portions of the articulating shafts in opposing directions.

In the depicted embodiment, the first and second cam profiles 104 and 106 are arranged symmetrically about the rotational axis of the articulation cam 102. Therefore, the first and second articulation pins 108 and 110, and associated articulating shafts 32 and 34, are displaced in opposing directions upon rotation of the articulation cam, see FIGS. 11-14. Additionally, the various portions of the first and second cam profiles 104 and 106 may be located at the same radial distances from the rotational axis of the articulation cam 102 which causes the first and second articulation pins 108 and 110, and associated articulating shafts 32 and 34 to be displaced by equal magnitudes in the opposing directions.

While a particular arrangement of the cam profiles has been illustrated it should be understood that other configurations may be suitable. For example, the cam profiles may not be symmetrically arranged around a rotational axis of the cam. In such an embodiment, the first profile portion 124, second profile portion 126, third profile portion 128, and fourth profile portion 130 may each be spaced at different radial distances from the rotational axis of the articulation cam 102. In other embodiments, one or both of the cam profiles may have only a single profile portion in which the spacing of the profile portion from the rotation axis varies along the length of the profile, or the cam profiles may have more than two profile portions as the disclosure is not so limited. Moreover, depending on the particular embodiment, the first, second, third, and/or fourth path portions of the first and second cam profiles may be located at respective constant radial distances from the rotational axis of the articulation cam, or the radial distances may not be constant and may vary within the respective path portions.

Figure 8:
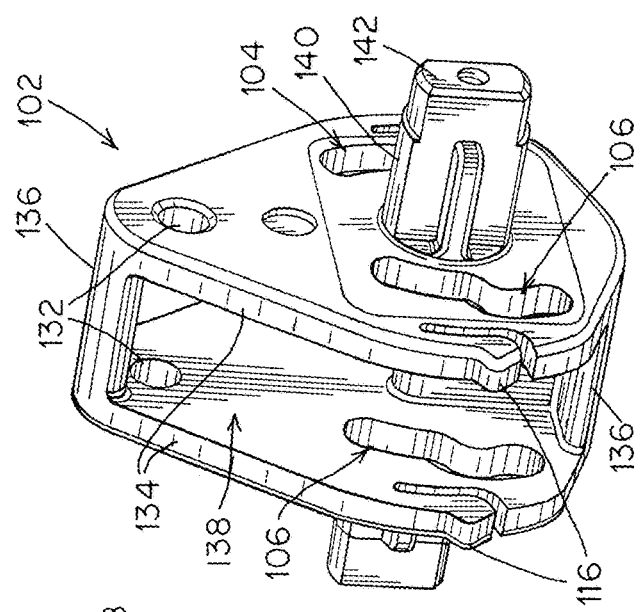
FIG. 8 is a perspective view of the articulation cam of FIG. 7.

As best illustrated in FIG. 8, the articulation cam may be constructed and arranged to accommodate various other components of a surgical instrument. For example, the articulation cam may include one or more channels, openings, or other feature to accommodate components of a power transmission system or a fastener deployment system that extend from a proximal portion of the device towards a distal end of an elongated shaft assembly. In the depicted embodiment, the articulation cam 102 includes a pair of end pieces 134 attached to one another with cross pieces 136 which define a channel 138 extending through the articulation cam. Each of the end pieces may include identical cam profiles 104 and 106. Additionally, the articulation cam may include a rotation shaft 140 extending from the end pieces that may include a keyed coupling 142 to attach an articulation control 10, such as a handle, to the articulation cam. However, other forms of attaching an articulation control to the cam including, but not limited to, welds, fasteners, snap fits, adhesives, and/or other appropriate attachment methods are also contemplated as the disclosure is not so limited.

In some embodiments, an articulation cam may be formed as a single monolithic component, for example, via a suitable molding or casting process. However, embodiments in which the articulation cam is formed from separate elements are also contemplated. For example, the various components, such as the end pieces and cross pieces may be formed separately and attached to one another with welds, fasteners, snap fits, adhesives, and/or other appropriate attachment methods as the disclosure is not so limited.

Figure 9:
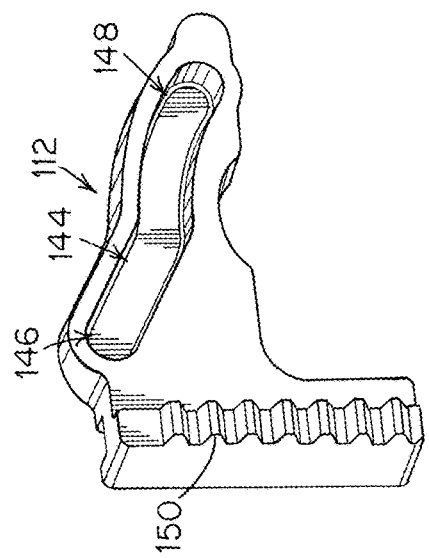
FIG. 9 is a perspective view of one embodiment of a locking cam.

FIG. 9 shows a schematic side view of a locking cam 112, which may be coupled to an articulation cam 102 and the locking shaft 36 as shown in FIG. 6. The locking cam includes a locking cam profile 144 constructed and arranged to receive a locking pin 152 (see FIG. 10) which is received within a through hole 132 of the corresponding articulation cam 102, see FIGS. 7-8. Accordingly, the locking pin 152 rotates at a constant radial distance from the rotational axis of the articulation cam 102 when the articulation cam is rotated. The locking cam 112 may be constrained to move in a desired direction, such as a direction transverse to a longitudinal axis of the elongated shaft assembly, to move the articulation lock to the unlocked configuration. Moreover, the locking cam profile 144 may include a fifth profile portion 146 constructed and arranged such that the rotational movement of the locking pin within the fifth profile portion causes the locking cam to move in the desired direction to displace the locking cam from a first position, which may correspond to the locking shaft 36 being in the locked configuration, to a second position corresponding to the locking shaft being in the unlocked configuration, see FIGS. 6 and 12. For example, in the depicted embodiment, the fifth profile portion is linear, though other configurations may be suitable.

The locking cam profile 144 of the locking cam 112 may further includes a sixth profile portion 148 that may be constructed and arranged such that movement of the locking pin 152 within the sixth profile portion does not cause any displacement of the locking cam. For example, the sixth profile portion may have a curved configuration such that, when the locking cam 112 is moved to the second position, the sixth profile portion 148 is located at a constant radial distance from the rotational axis of the articulation cam 102 that corresponds to the distance of the locking pin from the rotational axis. In this manner, a first portion of the movement of the articulation cam may cause movement of the locking cam, while the locking cam may remain stationary during a second portion of movement of the articulation cam.

In addition to the locking cam profile 144, the locking cam 112 may include a rack 150 that is constructed and arranged to engage a gear 114 which may be coupled to the locking shaft 36 of the elongated shaft assembly. The rack may extend in a direction that is parallel to a direction of movement of the locking cam. In this manner, displacement of the locking cam between the first position and the second position, may cause corresponding rotation of the gear and the locking shaft to move the locking shaft between the locked and unlocked configurations as previously discussed.

FIG. 10 is a schematic exploded view of an articulation control system 100, and illustrates how the various components of the articulation control system may be coupled to one another. As shown in the figure, the first articulation pin 108 is coupled to a proximal portion and/or end of the first articulating shaft 32 via a first shuttle 154 that is connected to the proximal portion and/or end of the first articulation shaft and first pin, and the second articulation pin 110 is coupled to a proximal portion and/or end of the second articulating shaft 34 via a second shuttle 156 connected to the proximal portion and/or end of the second articulation shaft and second pin. The first and second shuttles may be received within the channel 138 of the articulation cam 102 such that opposing ends of the articulation pins extend out from the shuttles and into the first and second cam profiles 104 and 106 located on either side of the articulation cam. Moreover, an end of a locking pin 152 of the articulation cam may extend out from, and in some embodiments, through the articulation cam such that the locking pin is received in the locking cam profile 144 of the locking cam 112 to couple the articulation cam to the locking cam.

Figure 11:
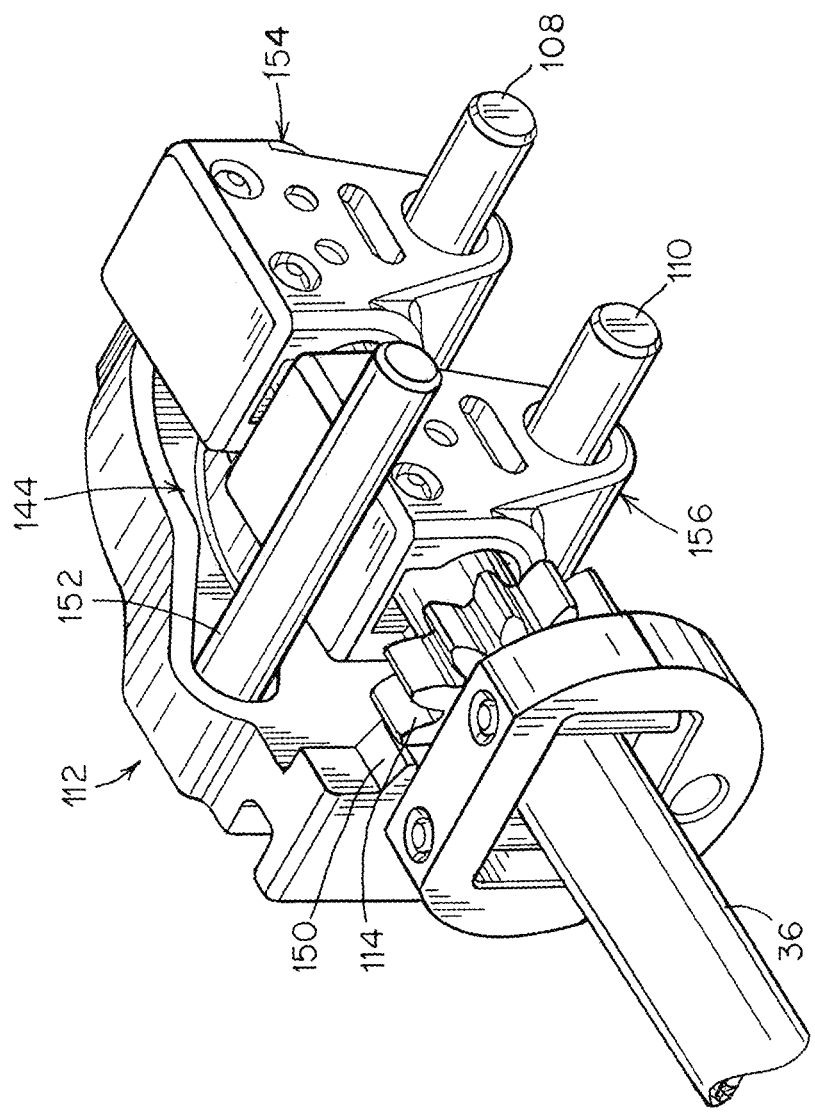
FIG. 11 is a perspective view of a portion of the articulation control system of FIG. 6 in the first position.

FIGS. 6 and 11-14 depict various aspects of the operation of the articulation control system 100. As discussed previously, FIG. 6 depicts the articulation control system 100 in a first position, corresponding to the elongated shaft assembly being in the non-articulated position and the locking shaft in the locked configuration. FIG. 11 shows a perspective view of the articulation control system in the first position, though for clarity, the articulation cam 102 is not depicted in FIG. 11. As illustrated, when the articulation control is in the first position, the first and second shuttles 154 and 156 may be located adjacent to one another and the locking pin 152 is received in a first end of locking cam profile 144. Moreover, when the locking cam is in the first position, a top portion of the locking cam rack 150 may be engaged with the gear 114.

Figure 13:
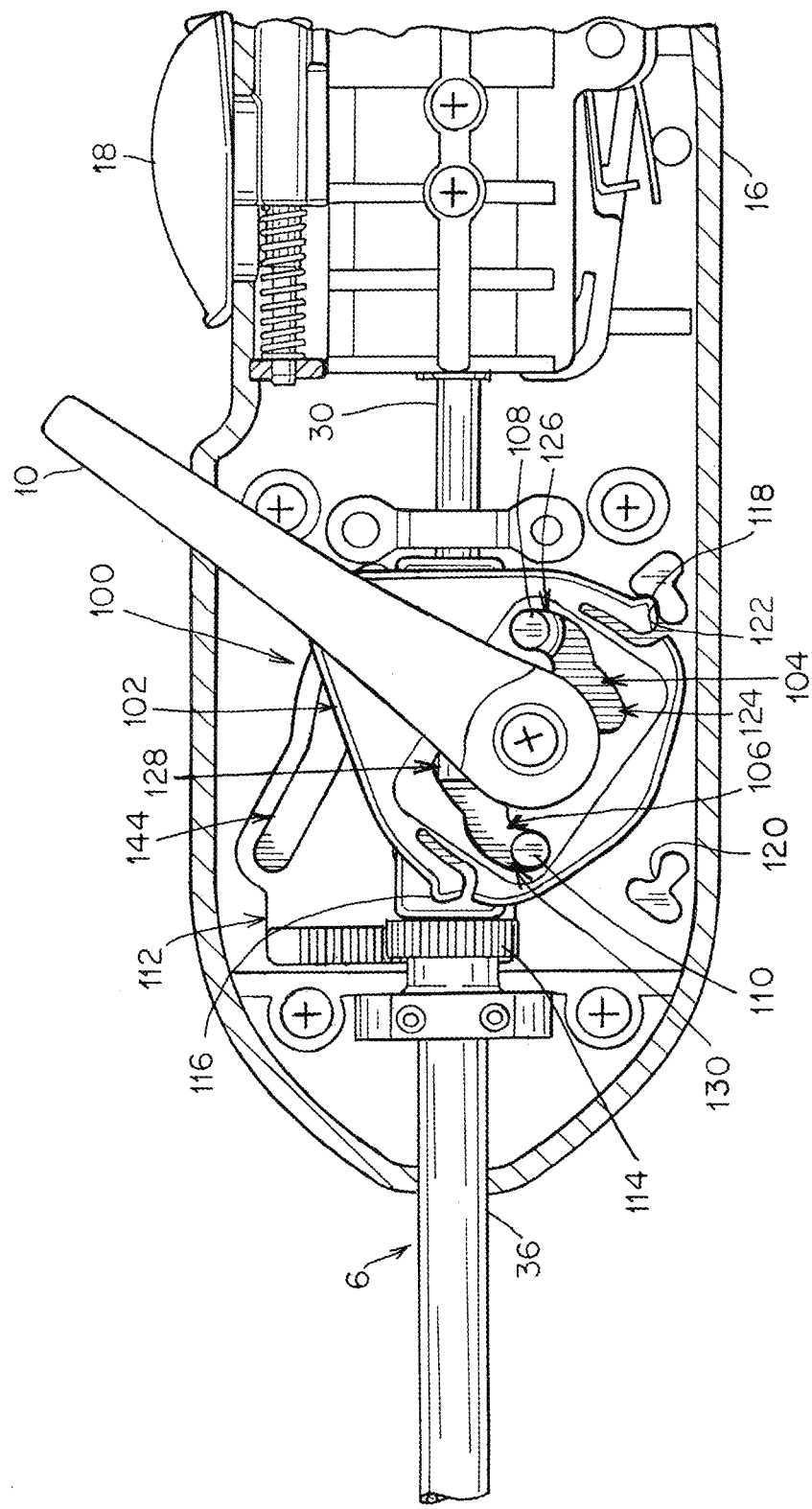
FIG. 13 is a side view of the articulation control system of FIG. 6 in a third position.
Figure 14:
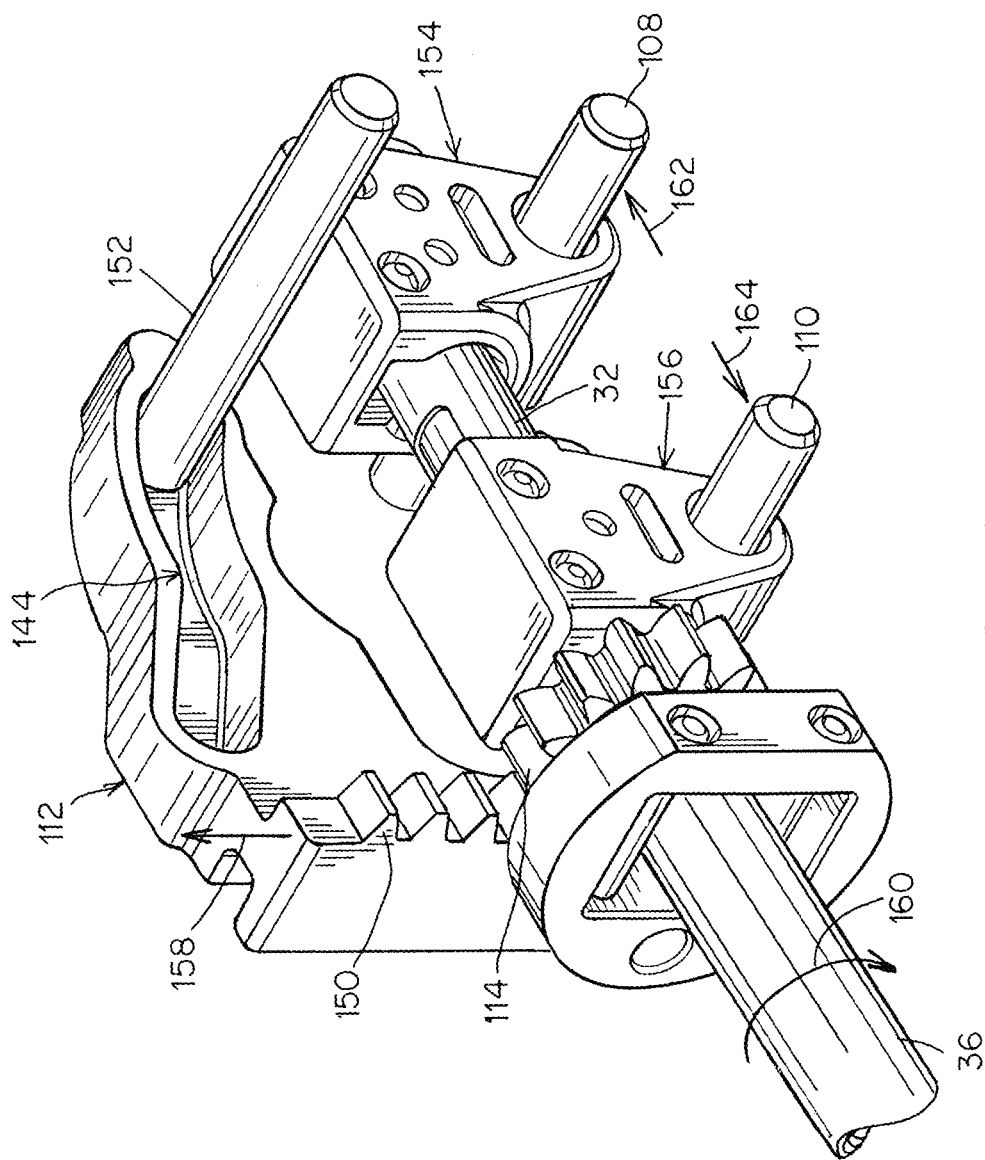
FIG. 14 is a perspective view of the portion of the articulation system of FIG. 11, with the articulation control system in a third position.

FIGS. 12-13 shows schematic side views of the articulation control system in a second position and a third position, respectively. For example, the second position may be an intermediate configuration corresponding to the locking shaft 36 being rotated to the unlocked configuration, but prior to articulation of the elongated shaft assembly such that the elongated shaft assembly is still in the non-articulated position. As shown in the figure, the articulation cam has been rotated relative to the configuration shown in FIG. 6, resulting in movement of the locking pin 152 within the locking cam profile 144 to the end of the fifth path portion 146 (and to the beginning of the sixth path portion 148). As discussed previously, movement of the locking pin within the fifth path portion may displace the locking cam 112 from the first position (shown in FIG. 6) to the second position shown in FIG. 12. This movement of the locking cam displaces the locking cam rack 150 which rotates the gear 114 and associated locking shaft 36 in direction 160 (FIG. 14). In the depicted embodiments, the displacement of the locking cam is in a direction 158 (FIG. 14) that is transverse to the longitudinal axis of the elongated shaft assembly, though other directions of movement and/or types of movement (such as rotational movement) also may be suitable, as the current disclosure is not limited in this regard.

As also shown in FIG. 12, when the articulation control system 100 is in the second configuration, the first and second articulation pins 108 and 112 are moved within the first and third path portions 124 and 128 of the first and second cam profiles 104 and 106, respectively. However, in some embodiments, the first and third path portions are located at constant radial distances from the rotational axis of the articulation cam. Thus, the articulation pins, and correspondingly, the elongated shaft assembly 6, remain stationary relative to the handle during movement of the articulation control system from the first position shown in FIG. 6 to the second position shown in FIG. 12. In this manner, moving the articulation control system from the first position to the second positon may move the locking shaft 36 from a locked configuration to an unlocked configuration while not applying any force to and/or displacing the articulating shafts which remain in the non-articulated configuration.

FIGS. 13 and 14 show the articulation control system 100 in a third position, where the locking shaft 36 is in the unlocked configuration and the elongated shaft assembly has been fully articulated. As illustrated in FIG. 13, the articulation cam 102 is further rotated relative to the second position shown in FIG. 12. This rotation causes the first and second articulation pins 108 and 110 to move within the first and second cam profiles 104 and 106 into the second and fourth profile portions 126 and 130, respectively. Since the second and fourth profile portions are located at different radial distances from the rotational axis of the articulation cam 102 relative to the first and third profile portions, the first and second articulation pins 108 and 110 are displaced in opposing directions either away from, or towards the rotational axis of the articulation cam. In particular, as shown in FIG. 14, the second and fourth profile portions are located a larger radial distance from the rotational axis of the articulation cam relative to the first and third profile portions. Accordingly, the first and second articulation pins 108 and 110, which may be constrained to move only axially as discussed below, are displaced in opposing axial directions. Specifically, the first articulation pin 108 is displaced in a proximal direction 162, and the second articulation pin is displaced in a distal direction 164. In some embodiments, the first and second cam profiles 104 and 106 may be arranged to cause displacements of the first and second articulation pins 108 and 110 that are equal in magnitude, which may aid in avoiding movement of the distal tip of the elongated shaft assembly, as discussed previously. However, in other embodiments, the displacements may not be equal in magnitude, as the disclosure is not limited in this regard.

Since the first and second articulation pins 108 and 110 are coupled to the proximal portions and/or ends of the first and second articulating shafts 32 and 34 via the first and second shuttles 154 and 156, respectively, the displacement of the articulation pins causes an associated displacement of the proximal ends of the articulating shafts. In particular the proximal end of the first articulating shaft 32 is displaced proximally along direction 162, and the proximal end of the second articulating shaft 34 is displaced distally along direction 164, see FIG. 14. Moreover, due to the attachment of the first and second shafts at the distally located attachment point 62 (see FIG. 5), the opposing displacements of the first and second articulating shafts places the shafts in opposing states of tension and compression, respectively. As discussed previously, these tensile and compressive states create a bending moment in the articulating shafts that causes the elongated shaft assembly to articulate toward the articulated position.

In addition to the movement of the articulation pins 108 and 110 within the second and fourth path portions 126 and 130, the locking pin 152 is moved within the sixth path portion 148 when the articulation control 100 is moved from the second position (FIG. 12) to the third position, see FIG. 13. However, as discussed above in connection with FIG. 9, when the locking cam is in the second position, which may correspond to the locking shaft being in the unlocked configuration, the sixth profile portion 148 of the locking cam may be located at a constant radial distance from the rotational axis of the articulation cam 102. Accordingly, movement of the locking pin within the sixth path portion may not cause any further movement of the locking cam, or any associated movement (e.g., rotation) of the locking shaft. In this manner, the locking shaft may remain in the unlocked position while the articulation control is moved between the second and third positions to articulate the elongated shaft assembly.

Although an articulation control system including various pins received in corresponding cam profiles is described above and shown in the figures, other configurations are also contemplated. For example, the articulation cam may include suitably shaped engaging surfaces that engage with corresponding surfaces on the articulating shafts and/or locking shaft to cause desired movement(s) of the shaft(s). Moreover, while a rotatable articulation cam is described above, other types of movement for the articulation cam may be suitable, as the current disclosure is not limited to surgical instruments in which an articulation cam is rotated to control articulation. For example, in certain embodiments, movement of the articulation control may displace the articulation cam relative to the handle of the surgical instrument, and the articulation may include suitably shaped camming structures to cause a desired displacement of the proximal portions of the articulating shafts.

Moreover, it should be understood that the articulation control systems described herein that control both articulation of an elongated shaft assembly movement of an articulation lock may be used with any suitable articulation system and/or locking system, as articulation control systems are not limited to the specific articulation and locking systems described herein. For example, the combined articulation and articulation lock control system may be used with articulation systems including elastically biased systems, flexible tubes and/or shafts, linked segments biased in one or more directions with one or more flexible members or cables placed into tension, and so on.

Figure 15:
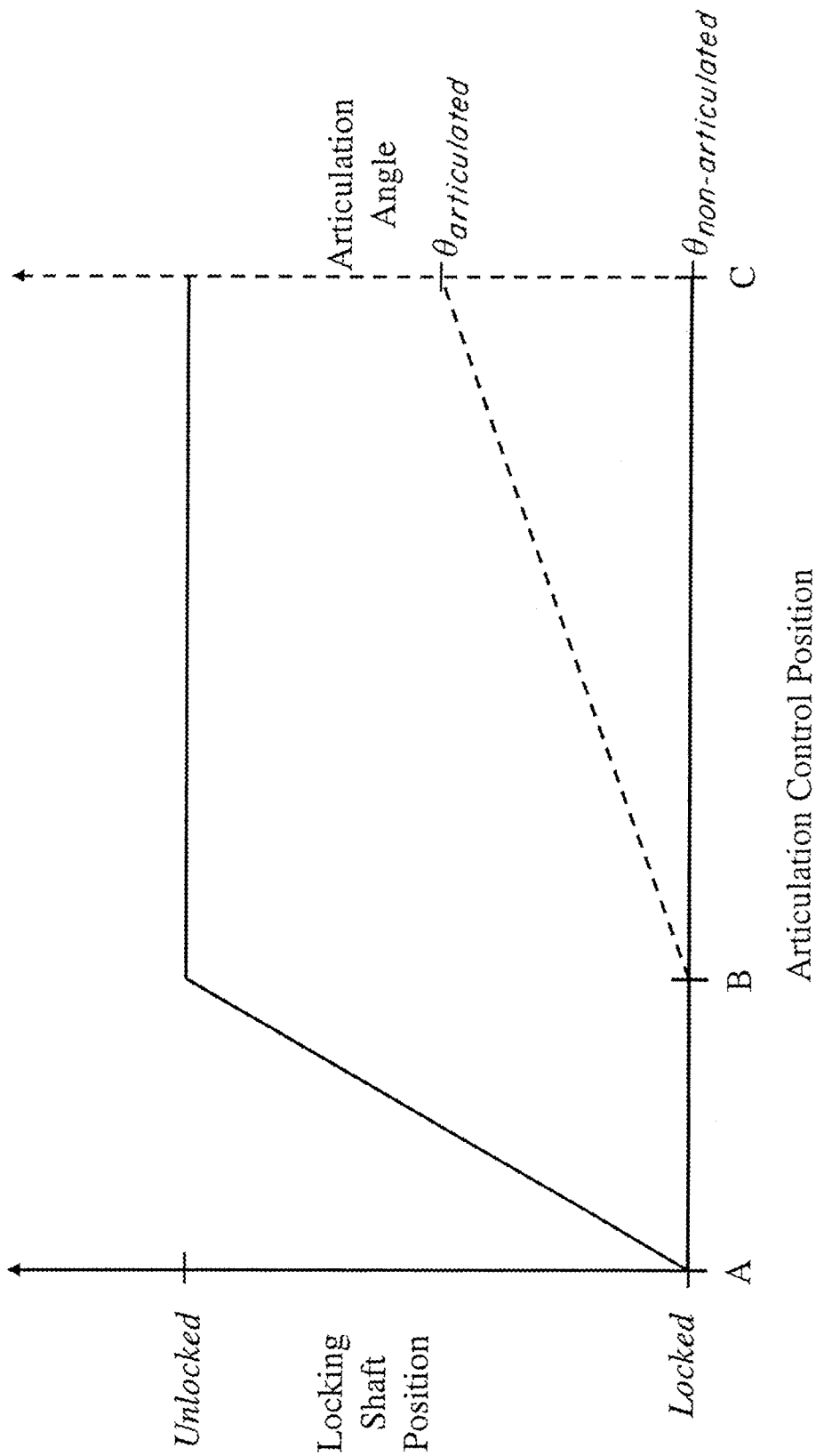
FIG. 15 is a schematic plot depicting movement of components of an articulation control system, according to one embodiment.

Referring now to FIG. 15, the operation of one embodiment of an articulation control system 100 and articulation lock described above in connection with FIGS. 6-14 is described in more detail. In particular, FIG. 15 is a schematic plot of the angular position of a locking shaft 36 as well as the articulation angle of the articulable portion of an elongated shaft assembly 6 relative to a proximal straight portion of the elongated shaft assembly as a function of the position of the articulation control 10. For example, position A may correspond to the first position of the articulation control system as illustrated in FIG. 6, i.e. an unarticulated position, in which the locking shaft is in the locked configuration and the elongated shaft assembly is in the non-articulated configuration. Correspondingly, position B may correspond to the second position of the articulation control system illustrated in FIG. 12 where the elongated shaft assembly has been unlocked and just prior to articulating the elongated shaft assembly. Position C may correspond to the third position of the articulation control system illustrated in FIG. 13 once the device has been fully articulated.

As illustrated in FIG. 15, when the articulation control is moved from position A to position B, the locking shaft moves from the locked configuration to the unlocked configuration. For example, in the embodiments described above in connection with FIGS. 6-14, the movement of the locking shaft may be a rotational movement. In particular, the locked configuration at position A may correspond to 0° of rotation such that the direction of bending resistance of the locking shaft is aligned with the preferential bending direction of the articulating shafts to prevent articulation of the elongated shaft assembly. Moving the articulation control from position A towards position B causes the locking shaft to rotate relative to the articulating shafts as described previously. This rotation may align one or more of the preferential bending directions of the locking shaft and articulating shafts to place the locking shaft and elongated shaft assembly in the unlocked configuration. This rotation may correspond to any appropriate angle, but in some embodiments, the unlocked configuration at position B may correspond to the locking shaft being rotated 90° relative to the locked configuration at position A.

While the locking shaft is moved from the locked position to the unlocked position during movement of the articulation control from position A to position B, the elongated shaft assembly does not articulate and remains in the non-articulated position. Specifically, the articulation angle remains at an angle of $\theta_{non\text{-}articulated}$, which may correspond to an articulation angle of 0°. Depending on the embodiment, this may be achieved via one or more suitably shaped cam profiles associated with the articulating shafts, such as those discussed above, which include at least one path portion located at a constant radial distance from a rotational axis or at a constant linear distance relative to a translational axis of the articulation cam depending on the type of cam movement. Accordingly, the pins, and thus the associated articulating shafts are not moved when the articulation control is moved from position A to position B.

When the articulation control is moved from position B to position C, the locking shaft may remain stationary in the unlocked configuration. For example, in the embodiments described above in connection with FIGS. 6-14, moving the articulation control handle from position B to position C may correspond to movement of the locking pin within the sixth path portion of the locking cam. As discussed previously, this portion of the locking cam may be located a constant radial distance from the rotational axis of the articulation cam when the locking cam is in the second position. As a result, moving the locking pin within this path portion may not cause any associated movement of the locking cam and may allow the locking shaft to remain in the locked position.

In addition to the above, moving the articulation control from position B to position C may cause the elongated shaft assembly to articulate from $\theta_{non\text{-}articulated}$ to an angle of $\theta_{articulated}$, which in some embodiments, may correspond to the elongated shaft assembly being moved to a fully articulated position. The specific articulation angle may correspond to any appropriate angle as described above. In some embodiments, such as those described above in connection with FIGS. 6-14, this articulation of the elongated shaft assembly may be caused by movement of the articulation pins within respective second and fourth path portions of the articulation cam, which are spaced a larger radial distance from the rotational axis of the articulation cam compared to the first and third path portions. Consequently, the articulation pins, and the associated proximal portions of the first and second articulating shafts, are displaced in opposing directions to place the articulating shafts in opposing states of tension and compression, thereby creating a bending moment to move the elongated shaft assembly to the articulated position. However, as discussed previously, other articulation mechanisms may be suitable, and correspondingly, moving the articulation control from position B to position C may cause an elongated shaft assembly in any suitable manner.

Although the articulation angle of $\theta_{articulated}$ is depicted in FIG. 15 as being smaller in magnitude than the angle corresponding to the locking shaft being in the unlocked position (e.g., 90°), other arrangements are also envisioned. For example, in some embodiments, the articulation angle of the elongated shaft assembly may be larger than the rotation angle required to move the locking shaft from the locked configuration to the unlocked configuration. Moreover, while the locking shaft rotation and elongated shaft assembly articulation are depicted as varying linearly with movement of the articulation control, the response may have any suitable functional form and may not be linear in some embodiments. In addition to the above, while in FIG. 15 there is no overlap in movement of the locking shaft and articulation of the elongated shaft assembly, other arrangements may be suitable. For example, in some embodiments, the elongated shaft assembly may begin articulating before the locking shaft is in the fully unlocked configuration as the disclosure is not so limited.

Figure 16:
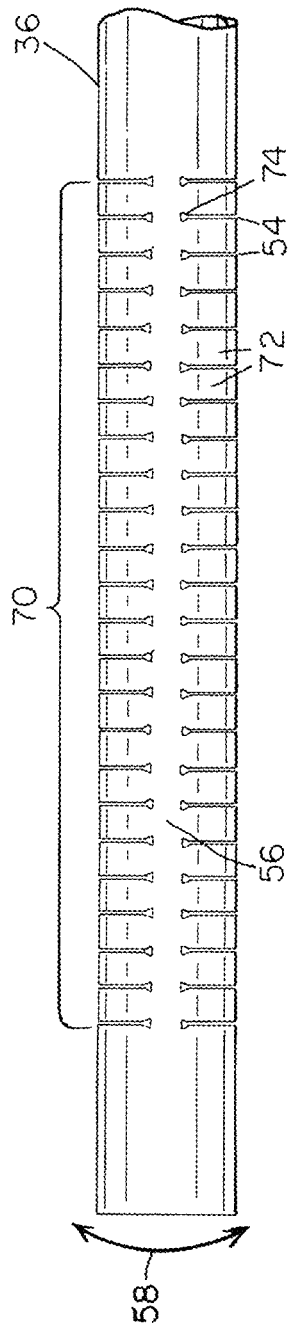
FIG. 16 is a side view of the locking shaft of the surgical instrument of FIG. 1.
Figure 17:
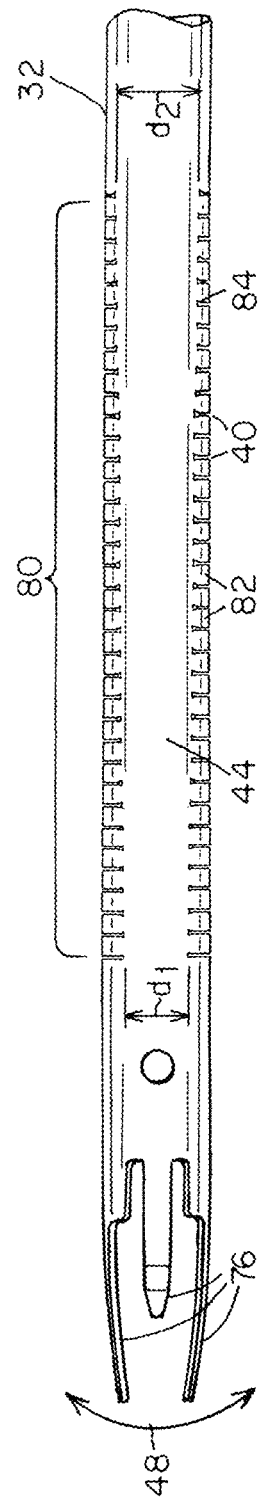
FIG. 17 is a side view of the first articulating shaft of the surgical instrument of FIG. 1.
Figure 18:
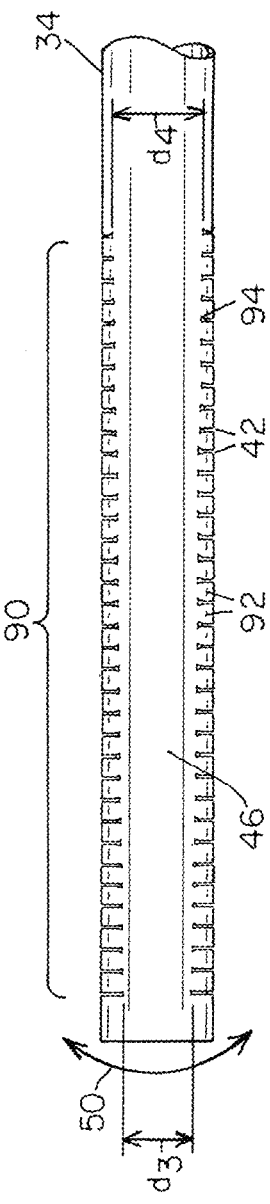
FIG. 18 is a side view of the second articulating shaft of the surgical instrument of FIG. 1.

Referring now to FIGS. 16-18, various aspects of the locking shaft 36 and the first and second articulating shafts 32 and 34 are described in more detail.

FIG. 16 depicts a schematic side view of a distal portion of a locking shaft 36. The locking shaft includes a pair of spines 56 located on opposing sides of the locking shaft (only one spine is depicted in FIG. 16) and the spines extend along the length of a flexible portion 70 of the locking shaft. The spines 56 correspond to a continuous portion of the locking shaft 36 and may be capable of transmitting axial forces along their length to the adjoining portions of the locking shaft. As discussed previously, the spines may be defined by a plurality of cuts 54 formed on opposing sides of the locking shaft within the flexible portion 70. For example the cuts may extend partially around the circumference of the locking shaft 36 and may be spaced apart axially along the length of the flexible portion 70 with the spines located between the opposing sets of cuts. The spines 56 and the cuts 54 may interact to form a plurality of flexible segments 72 joined together by a plurality of living hinges 74. Adjacent flexible segments 72 may pivot relative to one another about the intervening living hinges 74. This relative pivoting of the flexible segments may impart the flexibility to the locking shaft within the flexible portion 70. In addition, it is the orientation of the spines 56 and the cuts 54 that define the preferential bending direction 58 about an axis of rotation of the living hinges 74. Without wishing to be bound by theory, the living hinges 74 exhibit increased bending resistance in directions other than those corresponding to pivoting of the living hinges 74 about the axes of rotation of the living hinges. Thus, directions in which the living hinges 74 exhibit increased stiffness may be viewed as corresponding to directions of bending resistance (see FIG. 4). In the depicted embodiment, a direction of bending resistance 60 (FIG. 4) may correspond to a direction that is perpendicular to the preferential bending direction 58 and parallel to the axes of rotation of the living hinges 74 of the locking shaft 36.

FIG. 17 depicts a schematic side view of the distal end of a first articulating shaft 32, which may be an inner articulating shaft when arranged coaxially with a second articulating shaft 34 shown in FIG. 18. As discussed previously, the first articulating shaft includes a spine 44 extending along the length of a flexible portion 80 of the first articulating shaft. Similar to the above, the spine 44 corresponds to a continuous portion of the first articulating shaft 32 and may be capable of transmitting axial forces along its length to adjoining portions of the first articulating shaft, though unlike the locking shaft 36, the first articulating shaft has only a single spine 44. Moreover, the spine may be defined by a plurality of cuts 40 formed around a portion of the circumference of the first articulating shaft within the flexible portion 80, and the cuts may be spaced apart axially along the length of the flexible portion 80. Similar to the above, the spine 44 and the cuts 40 may interact to form a plurality of flexible segments 82 joined together by a plurality of living hinges 84. Adjacent flexible segments 82 may pivot relative to one another about the intervening living hinges 84. Without wishing to be bound by theory, the living hinges 84 exhibit increased bending resistance in directions other than those corresponding to pivoting of the living hinges 74 about the axes of rotation of the living hinges. This relative pivoting of the flexible segments may impart the flexibility to the first articulating shaft 32 within the flexible portion 80. Moreover, the orientation of the spine 44 and the cuts 40 define a preferential bending direction 48 parallel to the axes of rotation of the living hinges 84 of the first articulating shaft 32.

In addition, the first articulating shaft 32 may include one or more fastener retention features such as tabs 76 at the distal end of the first articulating shaft. Without wishing to be bound by theory, such tabs may aid in maintaining one or more fasteners at a desired position before or during deployment of fasteners from the surgical instrument.

Similar to FIG. 17, FIG. 18 depicts a schematic side view of the distal end of the second articulating shaft 34, which may be an outer articulating shaft when arranged coaxially with the first articulating shaft 32. Similar to the above, the second articulating shaft includes a spine 46 along the length of a flexible portion 90 of the second articulating shaft, and the spine 44 corresponds to a continuous portion of the second articulating shaft 34 that may be capable of transmitting axial forces along its length to adjoining portions of the second articulating shaft. The spine may be defined by a plurality of cuts 42 formed around a portion of the circumference of the second articulating shaft within the flexible portion 90, and the cuts may be spaced apart axially along the length of the flexible portion 90. Similar to the above, the spine 46 and the cuts 42 may interact to form a plurality of flexible segments 92 joined together by a plurality of living hinges 94. Adjacent flexible segments 92 may pivot relative to one another about the intervening living hinges 94. This relative pivoting of the flexible segments may impart the flexibility to the second articulating shaft 34 within the flexible portion 90. Moreover, the orientation of the spine 46 and the cuts 42 define the preferential bending direction 50 parallel to the axes of rotation of the living hinges 94.

When the first articulating shaft 32 and second articulating shaft 34 are assembled (e.g., coaxially arranged relative to one another as illustrated in FIGS. 4-5), the second articulating shaft may be rotated 180 degrees relative to the arrangement shown in FIG. 18, such that the spine 46 of the second articulating shaft is located on a side of the elongated shaft assembly that is opposite the spine 44 of the first articulating shaft 32. The inventors have recognized that locating the spines on opposing sides of the elongated shaft assembly may result in an increased stiffness for the elongated shaft assembly. As noted previously, such an increased stiffness may be advantageous to avoid undesired deflection or movement of the elongated shaft assembly, for instance, during actuation of the surgical instrument to deploy a fastener into tissue.

As illustrated in FIGS. 17 and 18, the spines 44 and 46 of the first and second articulating shafts 32 and 34, respectively, may have a tapered configuration. For example, the spine 44 of the first articulating shaft may have a first width $d_1$ at a distal end of the spine that is smaller than a second width $d_2$ at a proximal end of the spine 44. In some embodiments, the first width $d_1$ may be between about 1.5 mm and about 2.2 mm and the second width $d_2$ may be between about 3.5 mm and about 4.0 mm. Similarly, the second spine 46 of the second articulating shaft may have a third width $d_3$ at a distal end of the spine that is smaller than a fourth width $d_4$ at a proximal end of the spine 46. In some embodiments, the third width $d_3$ may be between about 2.6 mm and about 3.0 mm and the fourth width $d_4$ may be between about 4.3 mm and about 4.8 mm. Depending on the particular embodiment, the various cuts of the first and second articulating shafts may extend circumferentially between about 240 degrees and about 300 degrees the articulating shafts to define the tapered spine configurations. However, it should be noted that while specific ranges of dimensions are given herein for the cuts, spines, and other features, other ranges both larger and smaller than those disclosed herein may be used as the disclosure is not so limited.

Without wishing to be bound by theory, such a tapered configuration for the spines may impart enhanced flexibility to the flexible portions 80 and 90 at the distal ends thereof, while imparting progressively increasing rigidity towards the proximal ends. In this manner, the tapered spines may provide the articulating shafts with enhanced overall rigidity while still being flexible enough to permit articulation of the elongated shaft assembly. Moreover, in some embodiments, the tapered spines may provide for a more uniform rigidity along the length of the spines compared to a configuration with constant width spines. In particular, the increased width of the tapered spines in the proximal portions thereof may correspond to locations along the elongated shaft assembly that experience a larger bending moment compared to locations near the distal tip (e.g., due to a larger moment arm at locations further from the distal tip). Correspondingly, the increased rigidity of the tapered spines in these proximal locations may at least partially offset the larger bending moments, thus providing a more uniform bending rigidity along the length of the elongated shaft assembly.

Depending on the particular embodiment, the various cuts, spines, and flexible segments of the articulating shafts and/or locking shaft may have dimensions chosen to provide a desired rigidity and/or flexibility for the elongated shaft assembly. For example, the first and/or second articulating shafts may have diameters between about 3.5 mm and about 5.5 mm and a wall thickness between about 0.13 mm and about 0.30 mm, and the locking shaft may have a diameter between about 5.5 mm and 6.4 mm and a wall thickness between about 0.07 mm and about 0.15 mm. In one exemplary embodiment, the first articulating shaft has a diameter of about 4.8 mm and a wall thickness of about 0.025 mm, the second articulating shaft has a diameter of about 5 mm and wall thickness of about 0.18 mm, and the locking shaft has a diameter of about 5.6 mm and wall thickness of about 0.13 mm. Although the first and second articulating shafts and the locking shaft have different wall thicknesses in this embodiment, it should be understood that the current disclosure is not so limited. For instance, in other embodiments, the first articulating shaft may have a smaller wall thickness than the second articulating shaft and/or locking shaft, or the articulating shafts and locking shaft may have approximately the same wall thickness.

Moreover, in some embodiments, a spacing between adjacent cuts on the articulating shafts and locking shaft may be between about 0.6 mm and about 2.2 mm. In one exemplary embodiment, a spacing between adjacent cuts may be about 1 mm for the first and second articulating shafts, and about 1.5 mm for the locking shaft. Additionally, each of the first articulating shaft, second articulating shaft, and locking shaft may include cuts having different widths. For example, in one exemplary embodiment, the first articulating shaft has cuts with a width of about 0.007 mm to about 0.03 mm (e.g., about 0.02 mm), the second articulating shaft has cuts with a width of about 0.07 mm to about 0.18 mm (e.g., about 0.09 mm), and the locking shaft has cuts with a width of about 0.10 mm to about 0.18 mm (e.g., about 0.14 mm). In some embodiments, the width of the cuts on the locking shaft may be selected such that opposing sides of the cuts do not come into contact when the elongated shaft assembly is in a fully articulated configuration. For example, the inventors have found that such configurations may aid in permitting movement of the driveshaft (e.g., during deployment of a fastener) when the elongated shaft assembly is articulated. However, it should be understood that other dimensions for the spacing and width of the cuts, including ranges both smaller and larger than those noted above, may be suitable in some embodiments to provide a desired rigidity and/or flexibility of the elongated shaft assembly.

Depending on the embodiment, cuts formed in articulating and/or locking shafts may extend along a length of a flexible portion of each respective shaft in the articulable portion of the elongated shaft assembly. For example, in some embodiments, the length of the flexible portions of each shaft may be about 26 mm to about 42 mm. In some embodiments, the first and second articulating shafts may have flexible portions having the same length or different lengths. For example, the first articulating shaft may have a flexible portion with a length of about 26 mm to about 42 mm, and the second articulating shaft may have a flexible portion with a length of about 26 mm to about 38 mm. In certain embodiments, the lengths of the flexible portions of the first and second articulating shafts may be selected such that length of the flexible portion of the first shaft is equal to or longer than the length of the flexible portion of the second shaft.

In addition to the above, in some embodiments, and as shown in FIGS. 16-18, cuts formed in the various shafts may terminate in stress reliefs collocated with the living hinges. The stress reliefs may be shaped to aid in avoiding fatigue and/or failure of the living hinges upon repeated bending of the flexible portions, for example, when the elongated shaft assembly is moved back and forth between the non-articulated and articulated positions. In some embodiments, the stress reliefs may have an elliptical shape, though other shapes such as circles also may be suitable.

In addition to the above, while several patterns of cuts and spines are disclosed regarding the flexible portions of the locking shaft and articulating shafts, it should be understood that other patterns of cuts and spines are also possible. For example, the flexible portions of the shafts corresponding to the articulable portion of the elongated shaft assembly may be constructed and arranged in any appropriate fashion such that the flexible portion preferentially bends in at least one direction. Additionally, while spines with linear tapers have been depicted, embodiments in which the spines follow a non-linear taper are also contemplated.

Figure 19:
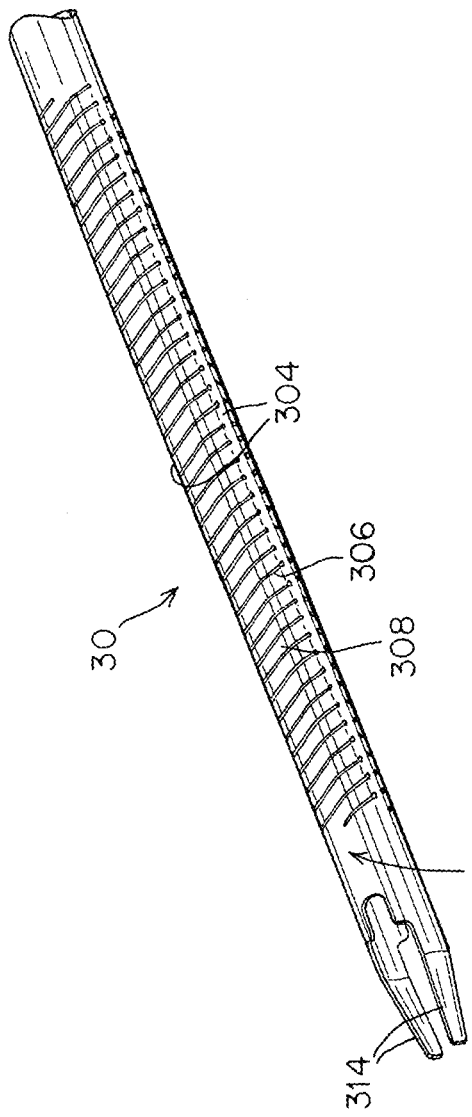
FIG. 19 is a perspective view of the driveshaft of the surgical instrument of FIG. 1.
Figure 20:
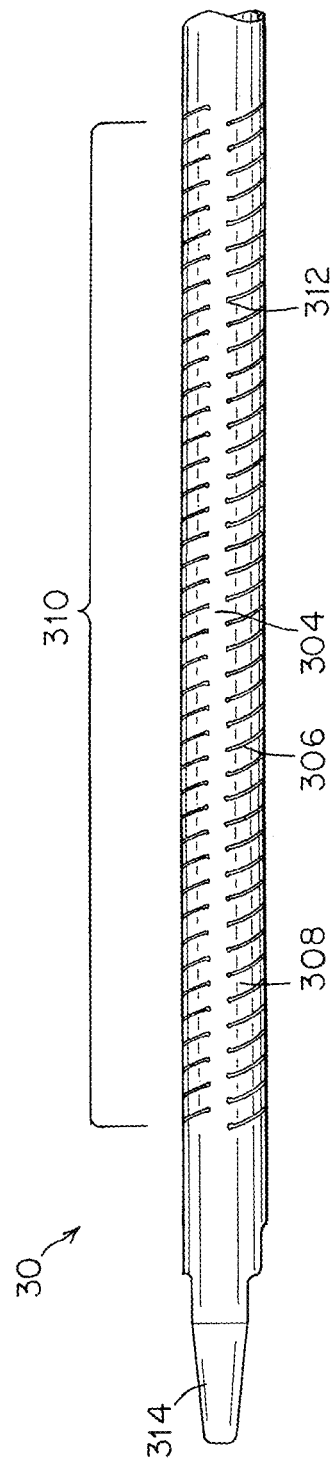
FIG. 20 is a side view of the driveshaft of FIG. 19.

FIGS. 19-20 depict one embodiment of a driveshaft 30 that may be employed in a surgical instrument to impart a distally directed force to deploy a fastener from the surgical instrument, for instance, via reciprocal axial displacement of the driveshaft. As shown in FIG. 3, the driveshaft may be coaxially arranged within the articulating shafts and the locking shaft, though other arrangements also may be suitable. In the depicted embodiment, the drive shaft includes a flat side 302 which may be constructed and arranged to engage a corresponding flat surface on the heads of the fasteners, as discussed in more detail below. The engagement of the flat surfaces may maintain the fasteners in a desired orientation within the driveshaft, including when the elongated shaft assembly is articulated. Moreover, the driveshaft may include a flexible portion 310 in which a pair of spines 304 are defined by a two plurality of cuts 306 extending partially around a circumference of the driveshaft and located on opposing sides of the driveshaft. The cuts are spaced along a length of the flexible portion similar to the locking shaft described above. Similar to the locking shaft, the spines 304 and the cuts 306 may interact to form a plurality of flexible segments 308 joined together by a plurality of living hinges 312, and adjacent flexible segments 308 may be pivoted relative to one another about the intervening living hinges 312.

As illustrated in FIGS. 19-20, the cuts may be arranged at a non-orthogonal angle relative to a longitudinal axis of the drive shaft. In some embodiments, the cuts may be arranged such that they follow a helical path around the driveshaft.

Without wishing to be bound by theory, this arrangement may place the cuts of the driveshaft 30 at an angle relative to the cuts located on the articulating shafts 32 and 34 which may aid in avoiding binding of the cuts on the driveshaft with the cuts on the articulating shafts. For example, any single angled cut 306 of the driveshaft would only contact an adjacent cut on the first locking shaft 32 at only a single point, thereby reducing the possibility of the cuts binding on one another as the driveshaft is displaced relative to the articulating shafts during deployment of a fastener.

Depending on the particular embodiment, the cuts on the driveshaft may have a width between about 0.07 mm and about 0.13 mm, and a spacing between adjacent cuts may be between about 0.8 mm and about 1.4 mm. In some embodiments, the cuts may define spines along the length of the driveshaft, and the spines may have a width ranging from about 0.5 mm to about 1.3 mm. Moreover, the cuts may extend along a flexible portion of the driveshaft, and the flexible portion may have a length of about 38 mm to about 54 mm. In certain embodiments, the length of the flexible portion of the driveshaft may be equal to or longer than a length of a flexible portion of an outer articulating shaft plus a travel distance of the driveshaft. Such a configuration may aid in permitting sliding of the driveshaft (e.g., during deployment of a fastener) while the elongated shaft assembly is in an articulated configuration.

In addition to the above, a driveshaft 30 may include fastener engaging features such as tabs 314 at a distal end of the driveshaft that extend in a distal direction and are oriented radially inwards. Therefore, when the trigger of the surgical fastener is actuated, the tabs may engage with a distal-most fastener to apply a distally directed force to the fastener to deploy the fastener from the distal end of the elongated shaft assembly. However, other configurations for applying a force to a distal most fastener are also envisioned as the disclosure is not so limited.

Figure 21:
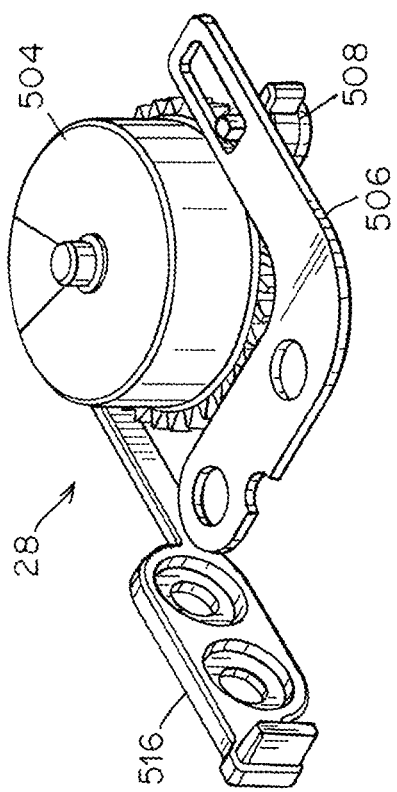
FIG. 21 is a rear perspective view of a portion of a surgical instrument.
Figure 22:
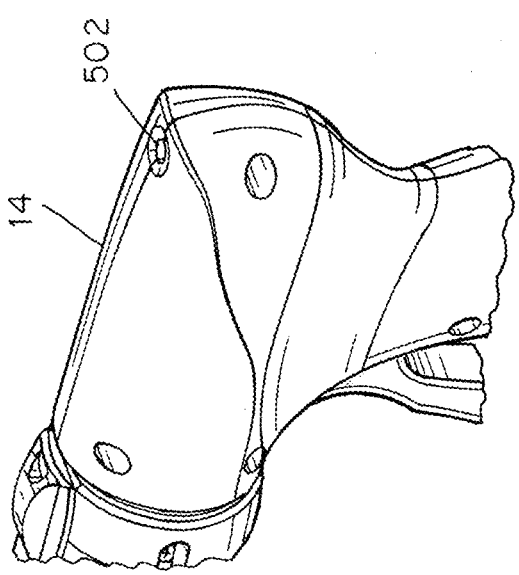
FIG. 22 is a perspective view of one embodiment of a fastener level indicator system.
Figure 23:
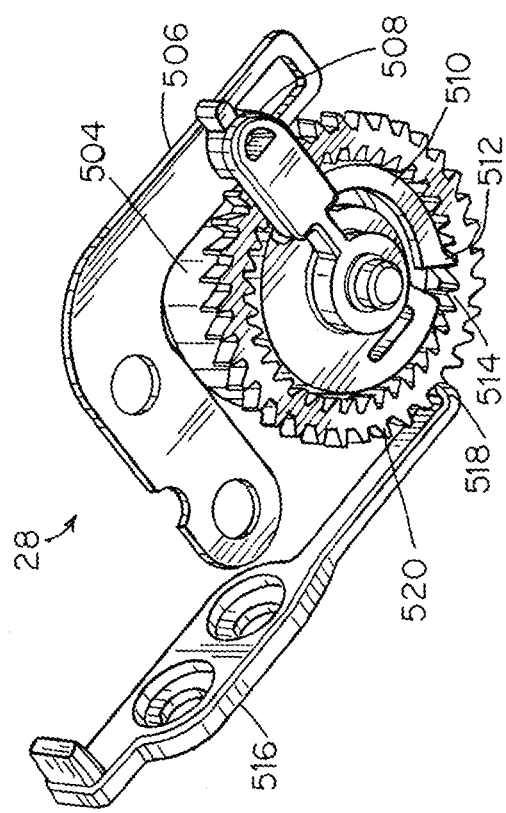
FIG. 23 is a perspective bottom view of the fastener level indicator system of FIG. 22.

Referring now to FIGS. 21-23, one embodiment of a fastener level indicator system 28 is described in more detail. As discussed previously, the fastener level indicator system may be constructed and arranged to provide an indication of the number of fasteners available for deployment from the surgical instrument. For example, FIG. 21 depicts a rear perspective view of a surgical instrument including a window 502 through which an indicator may be viewed. As shown in FIG. 22, the fastener level indicator system 28 may include an indicator 504 in the form of a gear cylinder. For instance, an upper surface of the indicator may be viewable through window 502. The indicator is coupled to a reciprocating arm 506, which may be coupled to the trigger 12 of the surgical instrument in any suitable manner such that upon actuation of the trigger (and deployment of a fastener), the reciprocating arm is moved to rotate the indicator to a new position. For example, the new position may indicate that one fewer fastener remains for deployment from the surgical instrument.

As illustrated in FIGS. 22-23, the reciprocating arm may be coupled to the indicator via an actuator 508 that is positioned within the gear cylinder of the indicator 504. As depicted in FIG. 23, which shows a perspective bottom view of the fastener level indicator system 28, the actuator 508 includes a resilient arm 508 with a tooth 512 at the end of the arm. The tooth 512 is constructed and arranged to engage corresponding gear teeth 514 located on the interior of the indicator gear cylinder 504. In this manner, the resilient arm and teeth 512 and 514 form a clutch-type interface between the actuator 508 and the indicator 504, such that rotation of the actuator in a first direction causes associated rotation of the indicator (e.g., to move the indicator to a new position), while rotation of the actuator in the opposite direction causes the resilient arm 510 to deflect inwardly such that the indicator is not rotated. Accordingly reciprocal movement of the reciprocal arm 506, which may cause associated rotation of the actuator in the first and second directions, does not cause the indicator to move backwards. Moreover, in some embodiments, the fastener level indicator system includes a stationary arm 516 that includes a tooth 518 constructed and arranged to engage corresponding teeth 520 formed on the outside of the indicator gear cylinder. The engagement of the teeth 516 and 520 may be arranged to block backwards rotation of the indicator.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A surgical instrument comprising:
   a handle;
   an elongated shaft assembly extending distally from the handle, the elongated shaft assembly including an articulable portion movable between a non-articulated configuration and an articulated configuration, the elongated shaft assembly comprising:
   a first shaft including an articulable portion having a first plurality of cuts spaced along a first length of at least a distal portion of the first shaft, wherein each cut of the first plurality of cuts extends partially around a circumference of the first shaft to define a first spine extending along the first length of the first shaft, the first spine having a first width at a distal end of the first spine and a second width greater than the first width at a proximal end of the first spine; and
   a second shaft coaxially arranged relative to the first shaft, the second shaft including an articulable portion having a second plurality of cuts spaced along a second length of at least a distal portion of the second shaft, wherein each cut of the second plurality of cuts extends partially around a circumference of the second shaft to define a second spine extending along the second length of the second shaft, the second spine having a third width at a distal end of the second spine and a fourth width greater than the third width at a proximal end of the second spine, wherein the first shaft and the second shaft are axially fixed at a location located distally from the articulable portion of the elongated shaft assembly, wherein the first spine is located on a first side of the elongated shaft assembly, wherein the second spine is located on a second opposing side of the elongated shaft assembly and opposite from the first spine, and wherein proximal portions of the first and second shafts are displaceable in opposing directions to articulate the elongated shaft assembly; and
   a driveshaft disposed within the first and second shafts, the driveshaft including a third plurality of cuts formed on the driveshaft, the third plurality of cuts spaced along at least a portion of a length of the driveshaft.

2. The surgical instrument of claim 1, wherein the first and second spines are parallel to a longitudinal axis of the elongated shaft assembly.

3. The surgical instrument of claim 1, wherein the first and second spines are curved along a length of the first and second shafts.

4. The surgical instrument of claim 1, wherein a width of each cut of the second plurality of cuts is selected such that opposing edges of each cut of the second plurality of cuts come into contact when the elongated shaft assembly is in the articulated configuration.

5. The surgical instrument of claim 1, wherein each cut of the third plurality of cuts forms at most one contact point with a cut of the first or second pluralities of cuts.

6. The surgical instrument of claim 5, wherein a width of each cut of the third plurality of cuts is selected such that opposing edges of each cut of the third plurality of cuts do not come into contact when the elongated shaft assembly is in the articulated configuration.

7. The surgical instrument of claim 1, wherein each cut of the first and second plurality of cuts has a width of between about 0.007 mm and about 0.018 mm.

8. The surgical instrument of claim 1, wherein a spacing between each cut of the first and second plurality of cuts is between about 0.6 mm and about 1.4 mm.

9. The surgical instrument of claim 1, wherein the first width is between 1.5 mm and about 2.2 mm and the second width is between about 3.5 mm and about 4.0 mm.

10. The surgical instrument of claim 1, wherein the third width is between about 2.6 mm and about 3.0 mm and the fourth width is between about 4.3 mm and about 4.8 mm.

11. A method of operating a surgical instrument, the method comprising:
articulating an articulable portion of an elongated shaft assembly between a non-articulated configuration and an articulated configuration, the elongated shaft assembly comprising:
a first shaft including an articulable portion with a first spine, the first spine having a first width at a distal end of the first spine and a second width greater than the first width at a proximal end of the first spine; and
a second shaft coaxially arranged relative to the first shaft, the second shaft including an articulable portion having a second spine, the second spine having a third width at a distal end of the second spine and a fourth width greater than the third width at a proximal end of the second spine, wherein the first spine is located on a first side of the elongated shaft assembly, wherein the first shaft and the second shaft are axially fixed at a location located distally from the articulable portion of the elongated shaft assembly, wherein the second spine is located on a second opposing side of the elongated shaft assembly and opposite from the first spine, and wherein proximal portions of the first and second shafts are displaceable in opposing directions to articulate the elongated shaft assembly, and
actuating a driveshaft disposed within the first and second shafts, the driveshaft including a plurality of driveshaft cuts formed on the driveshaft, the plurality of driveshaft cuts spaced along at least a portion of a length of the driveshaft.

12. The method of claim 11, wherein the first and second spines are parallel to a longitudinal axis of the elongated shaft assembly.

13. The method of claim 11, wherein the first and second spines are curved along a length of the first and second shafts.

14. The method of claim 11, wherein the first shaft includes a first plurality of cuts spaced along at least a distal portion of the first shaft, wherein each cut of the first plurality of cuts extends partially around a circumference of the first shaft to define the first spine, and wherein the second shaft includes a second plurality of cuts spaced along at least a distal portion of the second shaft, wherein each cut of the second plurality of cuts extends partially around a circumference of the second shaft to define the second spine.

15. The method of claim 14, further comprising contacting opposing edges of the second plurality of cuts when the elongated shaft assembly is in the articulated configuration.

16. The method of claim 14, further comprising: making at most one contact point between each cut of the plurality of driveshaft cuts and a cut of the first or second pluralities of cuts.

17. The method of claim 16, further comprising preventing contact between opposing edges of each cut of the plurality of driveshaft cuts when the elongated shaft assembly is in the articulated configuration.

18. A surgical instrument comprising:
a handle;
an elongated shaft assembly extending distally from the handle, the elongated shaft assembly including an articulable portion movable between a non-articulated configuration and an articulated configuration, the elongated shaft assembly comprising:
a first shaft including an articulable portion with a first spine, wherein a width of the first spine increases in a proximal direction; and
a second shaft coaxially arranged relative to the first shaft, the second shaft including an articulable portion having a second spine, wherein a width of the second spine increases in the proximal direction, wherein the first spine is located on a first side of the elongated shaft assembly, wherein the first shaft and the second shaft are axially fixed at a location located distally from the articulable portion of the elongated shaft assembly, wherein the second spine is located on a second opposing side of the elongated shaft assembly and opposite from the first spine, and wherein proximal portions of the first and second shafts are displaceable in opposing directions to articulate the elongated shaft assembly; and
a driveshaft disposed within the first and second shafts, the driveshaft including a plurality of driveshaft cuts formed on the driveshaft, the plurality of driveshaft cuts spaced along at least a portion of a length of the driveshaft.

19. The surgical instrument of claim 18, wherein the first and second spines are parallel to a longitudinal axis of the elongated shaft assembly.

20. The surgical instrument of claim 18, wherein the first and second spines are curved along a length of the first and second shafts.

21. The surgical instrument of claim 18, wherein the first shaft includes a first plurality of cuts spaced along at least a distal portion of the first shaft, wherein each cut of the first plurality of cuts extends partially around a circumference of the first shaft to define the first spine, and wherein the second shaft includes a second plurality of cuts spaced along at least a distal portion of the second shaft, wherein each cut of the second plurality of cuts extends partially around a circumference of the second shaft to define the second spine.

22. The surgical instrument of claim 21, wherein a width of each cut of the second plurality of cuts is selected such that opposing edges of each cut of the second plurality of cuts come into contact when the elongated shaft assembly is in the articulated configuration.

23. The surgical instrument of claim 21, wherein each cut of the plurality of driveshaft cuts forms at most one contact point with a cut of the first or second pluralities of cuts.

24. The surgical instrument of claim 23, wherein a width of each cut of the plurality of driveshaft cuts is selected such that opposing edges of each cut of the plurality of driveshaft cuts do not come into contact when the elongated shaft assembly is in the articulated configuration.

25. The surgical instrument of claim 21, wherein each cut of the first and second plurality of cuts has a width of between about 0.007 mm and about 0.018 mm.

26. The surgical instrument of claim 21, wherein a spacing between each cut of the first and second plurality of cuts is between about 0.6 mm and about 1.4 mm.

* * * * *